United States Patent [19]
Grevious et al.

[11] Patent Number: 5,752,977
[45] Date of Patent: May 19, 1998

[54] EFFICIENT HIGH DATA RATE TELEMETRY FORMAT FOR IMPLANTED MEDICAL DEVICE

[75] Inventors: John J. Grevious, Minneapolis; Robert A. Neumann, Blaine, both of Minn.; Koen J. Weijand, Hoensbroek, Netherlands

[73] Assignee: Medtronic, Inc., Minneapolis, Minn.

[21] Appl. No.: 842,581

[22] Filed: Apr. 15, 1997

[51] Int. Cl.$^6$ ................................................ A61N 1/37
[52] U.S. Cl. ................................................ 607/32
[58] Field of Search ...................... 607/32, 60; 128/903

[56] References Cited

U.S. PATENT DOCUMENTS

| | | |
|---|---|---|
| 4,550,370 | 10/1985 | Baker. |
| 4,556,063 | 12/1985 | Thompson et al.. |
| 4,571,589 | 2/1986 | Slocum et al.. |
| 5,127,404 | 7/1992 | Wyborny et al.. |
| 5,168,871 | 12/1992 | Grevious. |
| 5,292,343 | 3/1994 | Blanchette et al.. |
| 5,324,315 | 6/1994 | Grevious. |
| 5,354,319 | 10/1994 | Wyborny et al.. |
| 5,562,714 | 10/1996 | Grevious. |

*Primary Examiner*—William E. Kamm
*Attorney, Agent, or Firm*—Reed A. Duthler; Harold R. Patton

[57] ABSTRACT

A method and apparatus for transmitting information-encoded, telemetry signals percutaneously between an implanted medical device and an external device as telemetry RF pulses which are modulated in pulse position and/or in pulse width within a telemetry frame comprising at least a telemetry frame boundary RF pulse and a telemetry frame data RF pulse. Data to be transmitted in a given telemetry frame is encoded into a PPM code for positioning at least certain telemetry RF pulses at pulse positions of the telemetry frame and a PWM code for establishing the pulse widths of at least certain telemetry RF pulses of the telemetry frame. The telemetry frame is formatted from the PPM code, and the telemetry RF pulses are generated at the formatted pulse positions within the telemetry frame. The pulse widths of the telemetry RF pulses are controlled in accordance with the PWM code for the certain telemetry RF pulses. The PWM and PPM combinations of RF pulses of a telemetry frame can convey the data type, the telemetry frame frequency, number of pulse positions of the telemetry frame, data type and data content, including the identification of the implanted medical device. The selective PWM of certain or all RF pulses of the telemetry frame allows its data content to be increased or the telemetry frame size to be shortened or telemetry frame energy reduced by reducing the number of RF pulses of the telemetry frame or the range of possible pulse positions in the telemetry frame. The PWM may be reduced or disabled in noisy conditions.

42 Claims, 11 Drawing Sheets

EFFICIENT HIGH DATA RATE TELEMETRY FORMAT FOR IMPLANTED MEDICAL DEVICE

CROSS-REFERENCE TO RELATED APPLICATIONS

Reference is hereby made to commonly assigned, co-pending U.S. patent application Ser. No. 08/584,851 filed Jan. 11, 1996, now U.S. Pat. No. 5,683,432 for ADAPTIVE PERFORMANCE-OPTIMIZING COMMUNICATION SYSTEM FOR COMMUNICATING WITH AN IMPLANTED MEDICAL DEVICE in the names of S. Goedeke et al.; Ser. No. 08/768,605 filed Dec. 18, 1996, for IMPLANTABLE DEVICE TELEMETRY HIGH DATA TRANSMISSION RATE TELEMETRY TRANSMISSION FORMAT FOR IMPLANTED MEDICAL DEVICE in the names of J. Grevious et al.; and Ser. No. 08/813,963 filed Mar. 3, 1997 for METHOD AND APPARATUS FOR IMPLANTABLE MEDICAL DEVICE TELEMETRY in the names of J. Grevious et al, all of which contain related subject matter.

BACKGROUND OF THE INVENTION

1. Field of the Invention

The present invention generally relates to implantable medical devices, and more particularly, pertains to telemetry schemes for percutaneously transmitting analog and digital data from an implantable medical device at high data transmission rates combining pulse width modulation with pulse position modulation.

2. Description of the Prior Art

The earliest implantable medical devices, e.g., implantable cardiac pacemakers, were designed to operate in a typically single operating mode governed by fixed operating parameters without any ability to change the operating mode or otherwise communicate percutaneously with external equipment. In time, it became apparent that it would be clinically desirable to vary certain of the operating parameters and/or modes of operation. An initial approach employed with implanted cardiac pacemakers involved use of miniature rheostats that could be directly accessed by a needle-like tool inserted through the patient's skin to adjust a resistance in the pacing rate or pulse width setting circuit. Later, miniaturized reed switches were incorporated into the pacing rate or pulse width circuits that responded to magnetic fields applied through the skin by an external magnet placed over the implant site. The pulse width, pacing rate and a limited number of pacing modes could be adjusted in this manner.

It was also realized that the operation of an implantable cardiac pacemaker could be observed, for example, by use of a standard ECG machine and timing of intervals between pacing pulse spikes in the ECG tracing recorded from skin electrodes on the patient. Later, it became known that this technique could be used to detect data sent from the implanted cardiac pacemaker by modulating the pacing pulse amplitude, width or frequency in some manner. This approach could only provide a low bandpass data channel, of course, to avoid interfering with the primary function of pacing the patient's heart when necessary. One use of this technique was to monitor impending battery depletion through observation of a change in the pacing rate from a preset or programmed pacing rate in response to battery depletion.

As digital circuit technology advanced, it was recognized that control of operating modes and parameters of implanted medical devices could be realized in digital or binary circuits employing memorized control states or operating parameter values. In order to change an operating mode or parameter value, "programmers" were developed based on radio frequency (RF) downlink data communication from an external programmer transceiver to a telemetry transceiver and memory incorporated within the implantable pacemaker pulse generator. The operating modes and parameters that may be programmed are only limited by the designed capabilities of the implanted device.

It also became possible to provide uplink data telemetry to transmit the contents of a register or memory within the implanted pacemaker pulse generator to the telemetry receiver within the programmer employing the same RF transmission capabilities. Today, both analog and digital information or data can be transmitted by uplink RF telemetry from the implanted device to the external programmer. The analog information has typically included battery voltage, sampled intracardiac electrocardiogram amplitude values, sensor output signals, pacing pulse amplitude, energy, and pulse width, and pacing lead impedance. The digital information typically includes, statistics related to performance, event markers, current values of programmable parameters, implant data, and patient and pulse generator identifier codes. Similar analog and digital data is telemetered from implanted cardiac monitors, drug dispensers, cardioverter/defibrillators, and pacemaker/cardioverter/defibrillators.

Whenever data is encoded and transmitted from an implanted medical device, it consumes electrical current from the implanted device battery. The earliest RF telemetry systems transmitted analog and digital information in separate formats, resulting in inefficient utilization of the available power/bandwidth. Also, these modulation schemes tended to be less than satisfactory in terms of battery consumption, and did not lend themselves to simultaneous transmission of differing data types.

Many types of RF telemetry systems have been or currently are used in connection with implantable medical devices, such as cardiac pacemakers. An example of a pulse interval modulation telemetry system used for transmitting analog and digital data, individually and serially, from an implanted pacemaker to a remote programmer is disclosed in U.S. Pat. No. 4,556,063 issued to Thompson et al., incorporated herein by reference. A further example of a pacemaker programmer for use with programmable cardiac pacemakers having RF telemetry capabilities is disclosed in U.S. Pat. No. 4,550,370 issued to Baker, incorporated herein by reference. A further example of a pulse width modulation (PWM) telemetry system for transmitting binary "1" and "0" indicating pulse widths from an implanted cardiac pacemaker to an external programmer is described in U.S. Pat. No. 4,571,589, issued to Slocum et al., incorporated herein by reference.

An extensive description of the historical development of telemetry transmission formats and systems for both uplink telemetry of data from the implanted medical device to an external telemetry receiver and programmer and for downlink transmission of programming and telemetry trigger commands is set forth in the above-referenced '432 patent and in the following series of commonly assigned patents. Commonly assigned U.S. Pat. No. 5,127,404 to Wyborny et al., incorporated herein by reference, sets forth an improved method of telemetry frame based pulse position modulated (PPM) data transmission for uplink telemetry that increases bandwidth well above simple pulse interval or pulse width modulation binary bit stream transmissions. The details of this telemetry frame based, PPM telemetry data encoding system are set forth below in detail.

Commonly assigned U.S. Pat. No. 5,168,871 to Grevious et al., incorporated herein by reference, sets forth an improvement in the telemetry system of the '404 patent for detecting uplink telemetry RF pulse bursts that are corrupted in a noisy environment. Commonly assigned U.S. Pat. No. 5,292,343 to Blanchette et al., incorporated herein by reference, sets forth a further improvement in the telemetry system of the '404 patent employing a hand shake protocol for maintaining the communications link between the external programmer and the implanted medical device during slight variations in their relative positions caused by movement of the hand held programmer RF head. Commonly assigned U.S. Pat. No. 5,324,315 to Grevious, incorporated herein by reference, sets forth an improvement in the uplink telemetry system of the '404 patent for providing feedback to the programmer to aid in optimally positioning the programmer RF head over the implanted medical device involving the use of envelope modulation of the amplitudes of the RF carrier cycles in a downlink telemetry pulse. Commonly assigned U.S. Pat. No. 5,562,714 to Grevious, incorporated herein by reference, sets forth a further improvement in the programmer RF head for regulating the output level of the magnetic field of the transmission coil. Commonly assigned U.S. Pat. No. 5,354,319 to Wyborney et al., incorporated herein by reference, sets forth a number of further improvements in the telemetry frame based telemetry system of the '404 patent. Many of these improvements are incorporated into MEDTRONIC® Model 9760, 9766 and 9790 programmers.

The uplink telemetry RF pulses generated in these telemetry frame based telemetry systems are generally constant in pulse width. A fixed trigger or telemetry clock pulse is applied to the implanted device antenna circuit which momentarily couples battery voltage to the antenna L-C circuit. The L-C circuit responds by "ringing", generating a burst of damped sinusoidal, decaying amplitude RF cycles at the RF frequency, typically 175 kHz constituting the uplink telemetry RF pulse. The RLC time constant requires a minimum separation between telemetry clock pulses to ensure that the damped sinusoidal RF burst cycle amplitudes have decayed to baseline so that successive RF pulses, and the PPM spacing between them, can be decoded in the telemetry receiver. The downlink telemetry RF pulses are generated in somewhat the same manner and share the same general characteristics.

The telemetry frame based, PPM telemetry system disclosed in these patents increases the data transmission rate significantly over the simple bit stream telemetry transmission schemes using either PWM or PPM or pulse interval modulation (PIM) to distinguish a "1" from a "0" while diminishing consumption of battery current. A great deal of data may be encoded in a single telemetry frame and transmitted within the telemetry frame period defined by a discrete number of internal clock cycles. However, the RLC time constant and attendant minimum separation does limit the telemetry frame defining telemetry clock frequency. Moreover, in a "noisy" environment, stray electrical signals can be picked up by the RF head antenna and can corrupt the demodulated and decoded data.

As time passes, implanted medical devices become ever more complex in possible programmable operating modes, menus of available operating parameters, and capabilities of monitoring increasing varieties of physiologic conditions and electrical signals which place ever increasing demands on the programming system. It remains desirable to minimize the time spent in telemetry transmission both to reduce the likelihood that the telemetry link may be broken and to reduce current consumption. Consequently, a need remains for increasing the data transmission rate during uplink telemetry. As will become apparent from the following, the present invention satisfies that need.

SUMMARY OF THE INVENTION

The present invention provides a telemetry format combining a telemetry frame based, PPM telemetry format having a telemetry frame length defined by a certain number of clock cycles with PWM of certain ones or all of the RF pulses in the telemetry frame. The amount of data conveyed in the telemetry frame can be increased, if the number of clock cycles in the telemetry frame remains the same. Alternatively, the same amount of data can be conveyed in a telemetry frame that is shortened in the number of clock cycles. In either case, the data transmission rate is increased, thereby reducing the amount of energy expended, assuming no change in the total amount of data transmitted in the uplink telemetry transmission session. These embodiments of the invention are most advantageously employed in the uplink telemetry context, but may also be implemented in downlink telemetry of programming or interrogation commands.

In a preferred embodiment of the present invention, the PPM of the data to be transmitted is effected in the manner described in detail in the above-incorporated '404 patent and related patents. However, instead of the decaying RF carrier frequency pulse burst, a discrete number of constant amplitude, RF carrier frequency cycles are generated, wherein the RF pulse position within a range of possible positions in the telemetry frame and/or the number of carrier frequency cycles of the RF pulse, determining the overall pulse width, identify a data value, a telemetry frame type, the telemetry clock frequency, the implantable device, or any other attribute of the telemetered data.

In one simplified preferred embodiment, a method and system for transmitting information-encoded, telemetry signals percutaneously between an implanted medical device and an external device as telemetry RF pulses within a telemetry frame comprises the steps of and means for: providing a source of data to be transmitted; encoding the data into a PPM code for positioning at least certain telemetry RF pulses at pulse positions of the telemetry frame and a PWM code for establishing the pulse widths of at least certain telemetry RF pulses of the telemetry frame; formatting the telemetry frame from the PPM code; generating the telemetry RF pulses at the formatted pulse positions within the telemetry frame; and controlling the pulse widths of the telemetry RF pulses in accordance with the PWM code for the selected telemetry RF pulses.

Preferably, the telemetry frame comprises at least one telemetry frame boundary RF pulse and optimally a telemetry frame synchronization RF pulse, formatted in a fixed relative time relationship so that the telemetry frame may be identified by demodulation of the transmitted RF pulses and the fixed time relationship between them, and at least one data RF pulse positioned in the telemetry frame with respect to the telemetry frame boundary RF pulse in accordance with the PPM code. The telemetry frame may optionally include more than one data RF pulse that is also positioned in the telemetry frame with respect to the telemetry frame boundary RF pulse in accordance with the PPM code. The PWM of at least one of the telemetry frame boundary RF pulse, the telemetry frame synchronization RF pulse and the data RF pulse(s) may be employed to identify the telemetry frame length (i.e., the number of RF data pulses in the telemetry frame), the telemetry clock frequency, the telemetry frame type, or to convey additional data of the telemetry frame. The telemetry frame may also include a separate identifier RF pulse that is positioned in the telemetry frame with respect to the telemetry frame boundary RF pulse to identify the type of data encoded into the telemetry frame or other characteristics of the telemetry frame or the implanted medical device which may also be timed in pulse width in accordance with a PWM code. The telemetry frame optionally includes additional RF pulses that are fixed in position or positioned in accordance with a related PPM code for the telemetry frame with respect to the telemetry frame boundary RF pulse or another RF pulse of the telemetry frame. Any one or all of the RF pulses of the telemetry frame may be pulse width modulated in accordance with a PWM code.

In accordance with a comprehensive preferred embodiment, an apparatus for transmitting information-encoded, telemetry RF pulses percutaneously between an implanted medical device and an external device comprises: a data bit source for telemetry frame identifier and data to be transmitted in a telemetry frame; a data encoder for encoding the telemetry frame identifier and data of each telemetry frame into RF pulse width defining code and RF pulse position defining code; clock means for providing telemetry clock signals at preset clock intervals for use in defining pulse positions of the telemetry frame; a telemetry frame formatter responsive to the clock means and the data-encoded RF pulse position defining code for generating RF pulse trigger signals at a telemetry frame boundary RF pulse position, a synchronization RF pulse position, an encoded telemetry frame identifier RF pulse position within a telemetry frame identifier range of possible telemetry frame identifier RF pulse positions, and at least one encoded data RF pulse position within a data range of possible data RF pulse positions; an RF pulse generator responsive to the RF pulse trigger signals for generating an RF pulse at each of the telemetry frame boundary RF pulse position, the synchronization RF pulse position, the telemetry frame identifier RF pulse position, and the data RF pulse position; and an RF pulse width controller responsive to the data-encoded pulse width defining code from the data encoder for controlling the RF pulse width in each or in selected ones of the telemetry frame boundary, the synchronization, the telemetry frame identifier, and the data RF pulse positions. Preferably, the telemetry frame is formatted to include the telemetry frame identifier RF pulse in a telemetry frame identifier range identifying the type of data transmitted in the telemetry frame and to include a plurality of data RF pulse ranges within which a corresponding plurality of the data RF pulses may be positioned.

In a further aspect of the present invention, it is contemplated that the use of the PWM of the RF pulses of the telemetry frame of the present invention may be implemented into the telemetry transmission hardware and software of implanted medical devices such that the PWM feature may be selectively enabled and disabled, depending on the capability of the external programmer and/or on ambient conditions. If it is not possible to decode the uplink telemetry in the presence of interference or for any other reason, it is contemplated that the external programmer can command the implanted device to revert to a pre-existing fixed RF pulse width telemetry format or to employ fewer pulse widths that are more readily distinguishable.

The use of the PPM telemetry frame-based telemetry format and capability of encoding more data into a single RF pulse also decreases the overall battery current requirements and serves to level the energy demand over time. In the context of cardiac medical devices, the transmission protocol provides data rates which are sufficient to transfer clinically useful EGM information in real time. Because each telemetry frame is independent, data quantities of varying precision can be transmitted using the same protocol.

BRIEF DESCRIPTION OF THE DRAWINGS

The present invention will be better understood, and its attendant advantages will be readily appreciated, by reference to the accompanying drawings when taken in consideration with the following detailed description, wherein.

DETAILED DESCRIPTION OF THE PREFERRED EMBODIMENTS

A preferred embodiment of the present invention is disclosed relating to use of the improved uplink telemetry format and protocol between an implanted cardiac pacemaker pulse generator, which may be programmable, and an external programmer of the types described above as illustrated in FIG. 1. However, those of skill in the art will be readily able to adapt the teachings found herein to other implantable medical devices. It will also be understood by those of skill in the art that the telemetry format taught herein can be used for bi-directional communications (i.e., uplink and downlink telemetry) between an implanted medical device and an external device. Moreover, while the present invention is preferably implemented into the telemetry frame based telemetry format of the above-incorporated '404 and '319 patents for ease of implementation and to increase its data transmission rate, it will be understood that these benefits may also be applied to other simpler or more complex pulse position modulated data transmission formats that may be characterized as telemetry frame based.

Figure 1:
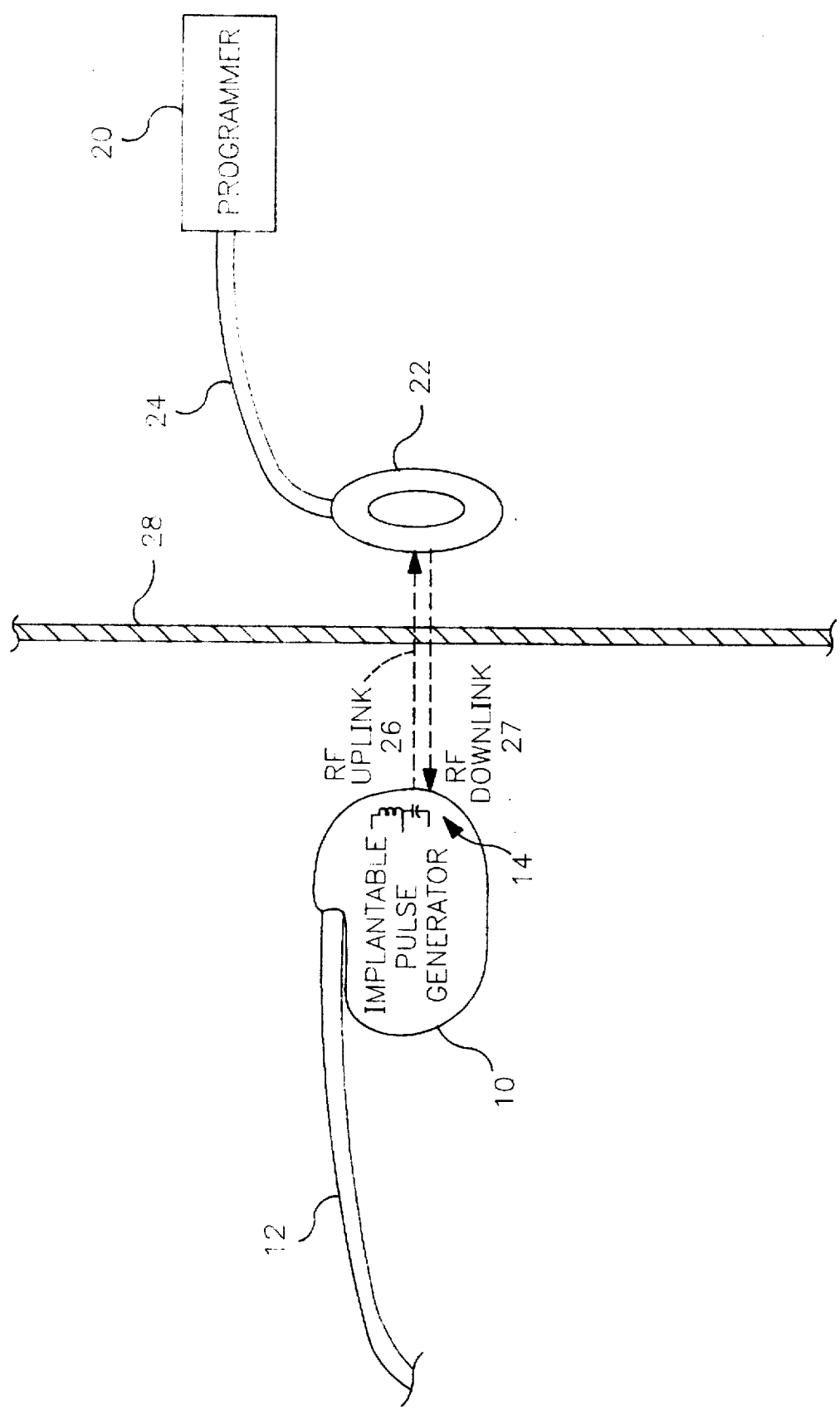
FIG. 1 is a simplified schematic view of an implanted medical device in relation to an external medical device between which telemetry uplinks and downlinks are established providing two way telemetry communication in which the improved telemetry format of the present invention may be utilized.

FIG. 1 is a simplified schematic diagram of the bi-directional communication between an external programmer 20 and an implanted medical device, e.g., a cardiac pacemaker implantable pulse generator (IPG)10. The IPG 10 is implanted in the patient beneath the skin barrier 28 and is electrically coupled to the heart of the patient using at least one cardiac pacing lead 12 in a manner known in the art. Percutaneous telemetry data is transmitted from an implanted medical device or IPG RF antenna 14 within IPG 10 by an RF uplink 26, utilizing the improved telemetry format of the present invention, to a an RF head antenna 22 included within a hand held programmer RF head (not shown) which is coupled to a programmer 20 via a cable 24. The programmer RF head also may contain a magnet which activates a reed switch in IPG 10 as a safety feature, as taught in U.S. Pat. No. 4,006,086 issued to Alferness et al., herein incorporated by reference, and INTERROGATE and PROGRAM push-buttons. The telemetered out RF pulses in each telemetry frame are detected, demodulated, decoded into a human readable language, recorded in memory, and displayed on a display screen or printed out for the attending medical personnel by programmer 20. In accordance with the present invention, the demodulation includes the determination of the pulse width modulation, and the decoding determines a data type identification, a data value, a telemetry frame size, etc., from the combination of the PWM with the decoded PPM of the RF pulse in a respective range within the telemetry frame.

Percutaneous downlink telemetry of interrogation commands and programming commands generated by the external programmer 20 are communicated to IPG RF antenna 14 in the IPG 10 in an RF downlink 27. In accordance with one aspect of the present invention, the RF uplink signal strength is evaluated in the manner described in the above-referenced '851 application, incorporated by reference herein. Closed loop control of the formatting of the RF uplink 26 is effected in the manner disclosed therein.

When the RF uplink signal strength is weak and/or noise levels are high resulting in difficulty in accurately detecting and demodulating the pulse widths of the RF pulses of the uplink telemetry frame, the PWM scheme is altered in order to continue with the RF uplink 26. The IPG 10 may be instructed by the programmer 20 in an RF downlink command to format RF uplink telemetry frames using a lesser number and more distinguishable pulse widths or eliminating the PWM entirely.

Figure 2:
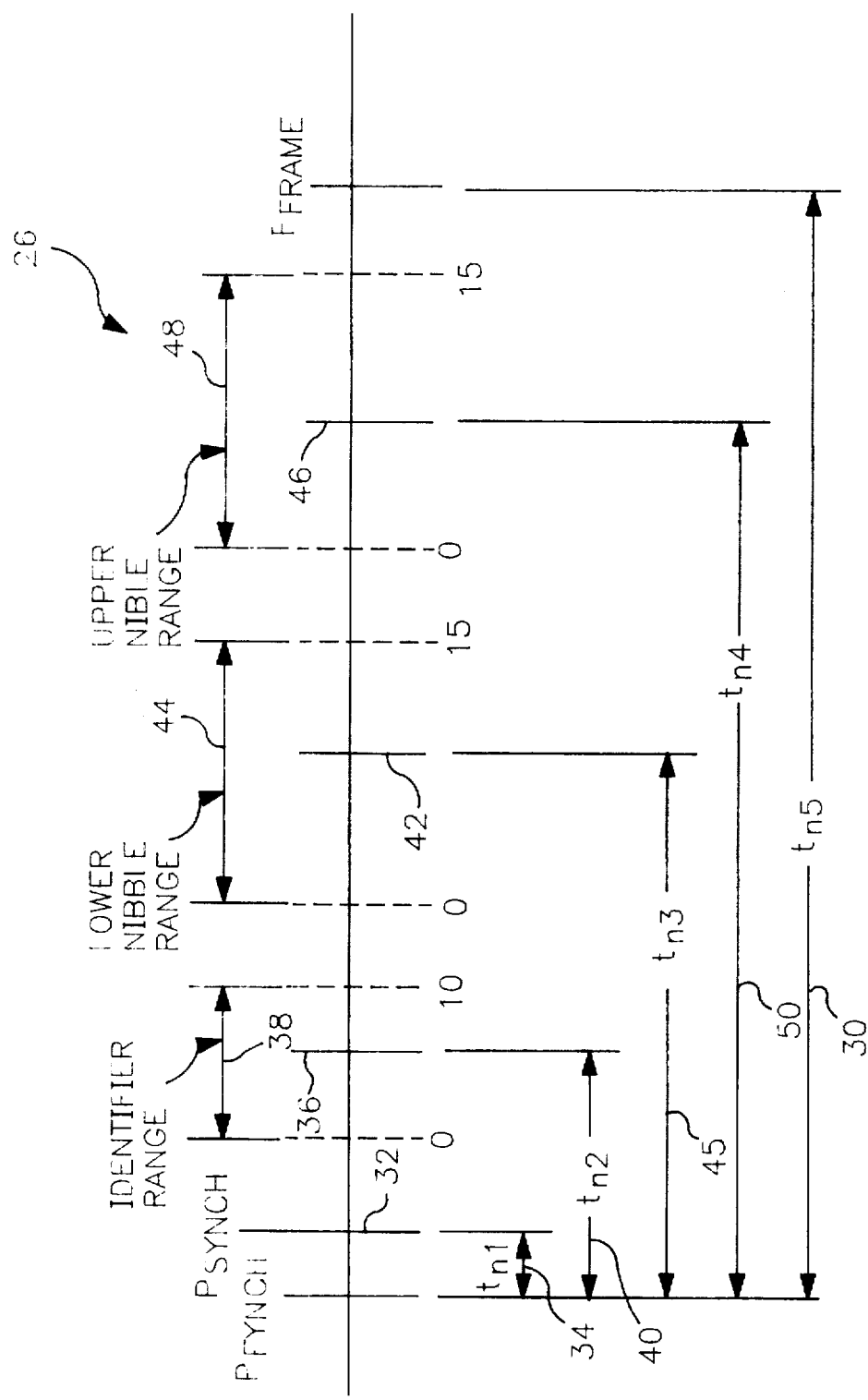
FIG. 2 is a conceptual view of an exemplary telemetry frame illustrating the PPM of the RF pulses of the telemetry frame in which the PWM of the present invention is preferably implemented.

FIG. 2 is a schematic diagram of the protocol of RF uplink 26 using the telemetry frame based and pulse width modulation improved telemetry format of the present invention. The uplink 26 uses a number of 175 kHz RF carrier pulses which are pulse position modulated and at least certain of which are pulse width modulated, as described in detail below, within a telemetry frame 30. The telemetry frame 30 constitutes the basic telemetry timing unit of the uplink 26, the telemetry frame having a time duration of $t_{n5}$ elapsed from a telemetry frame start pulse $P_{TELEMETRY\ FRAME}$ and corresponding to a predetermined number of clock pulses. In the preferred embodiment, a primary timing generator of IPG 10 comprises a standard 32.768 kilohertz crystal clock which provides a basic clock cycle of 30.52 microseconds. Thus, as described in the above-incorporated '404 patent, a telemetry frame 30 comprised of 64 clock cycles and extending over a fixed time interval of 1.953125 msec is a convenient telemetry frame period, since such telemetry frame period is a binary multiple of the basic clock cycle.

As described further below, assuming a 64 telemetry clock telemetry frame and the same number of RF pulses in the telemetry frame 30, the PWM encoding of at least certain of the RF pulses allows the telemetry frame data transmission rate to be magnified in proportion to the number of pulse widths employed in the PWM, the number of the RF pulses of the telemetry frame that are PWM encoded and the number of possible pulse positions of the range of PPM of the respective RF pulse. Alternatively, the same amount of data encoded simply using PPM in a 64 cycle telemetry frame 30 can be encoded in a telemetry frame 30 comprised of far fewer clock cycles using both PPM and PWM of certain or all of the RF pulses.

Moreover, the substitution of discrete pulse width RF pulses for the damped sinusoidal RF pulses of the telemetry frame described in the above-incorporated '404 and '319 patents facilitates the use of a higher frequency clock, e.g., 100 kHz, which can increase the data transmission rate, because the RF pulse width can be controlled more precisely. The RF cycle controlling circuits disclosed in the above-incorporated '605 application are preferably used in the implementation of the present invention to precisely stop the RF pulse at the end of each cycle (or half cycle). As described in greater detail below, the PPM encoding may employ a number of pulse widths, e.g., 4, 5, 6, 7, etc., RF carrier cycles. Consequently, the amount of data bytes that may be transmitted in a given telemetry frame may be magnified considerably.

Returning to FIG. 2, the pulse positions and pulse position ranges of an exemplary telemetry frame of the type described in the above-incorporated '404 and '319 patents will first be explained. Assuming a 64 clock cycle telemetry frame, the telemetry frame 30 is divided up into a sequence of non-overlapping, sub-interval ranges of a discrete number of clock cycles, i.e., pulse positions, separated by guard bands of a further number of clock cycles. A synchronization RF pulse 32 is positioned within telemetry frame 30 at a time $t_{n1}$ measured from the telemetry frame boundary or start RF pulse $P_{TELEMETRY\ FRAME}$. In order to decode the beginning (or end) of a telemetry synchronization RF pulse 32 must always be located at the end of the fixed time $t_{n1}$ within the telemetry frame 30, as shown at 34, as measured from the telemetry frame boundary or start RF pulse $P_{TELEMETRY\ FRAME}$.

After a guard band of clock cycles elapsing from synchronization RF pulse 32, an identifier (ID) sub-interval range 38 of each telemetry frame 30 is defined. ID range 38 uses a total of M clock cycles as shown, where M is selected to be 11 in the telemetry frame example of FIG. 2. In accordance with one embodiment of the present invention, the identification of the data being transmitted in this telemetry frame is imparted by: (1) the position 40 or time interval $t_{n2}$ of ID RF pulse 36 within ID range 38; and/or (2) the pulse width modulation of the ID RF pulse 36. If the PWM or PPM of the ID RF pulse is sufficient to identify the nature or type of data found within telemetry frame 30, then the PPM or PWM, respectively, may be used to convey a data value bit.

In a first example, each telemetry frame 30 is pulse position encoded from one eight-bit data byte. A first four-bit portion of this PPM data byte, namely the four least significant bits, is position encoded to define a position at time $t_{n3}$ (shown at 45) within a fixed, "lower nibble" (LN) range 40 of telemetry frame 30. The LN data RF pulse 42 is generated by an RF pulse generator when the telemetry clock times out the time (or number of telemetry clock pulses) $t_{n3}$ as described below. In accordance with the present invention, the pulse width of the LN data RF pulse is controlled in accordance with the LN PWM data which may comprise 1 or 2 bits to define up to four pulse widths.

Similarly, the second four-bit portion of this PPM data byte, namely the four most significant bits, is position encoded to define a position at time $t_{n4}$ (shown at 50) within a fixed, "upper nibble" (UN) range 48 of telemetry frame 30. The UN data RF pulse 46 is generated in an RF pulse generator when the telemetry clock times out the time (or number of telemetry clock pulses) $t_{n4}$ as described below. In accordance with the present invention, the pulse width of the UN data RF pulse is controlled in accordance with the UN PWM data which may comprise 1 or 2 bits to define up to four pulse widths.

LN range 44 and UN range 48 each therefore comprise 16 telemetry clock determined telemetry frame positions, permitting each of the sixteen unique values of the four-bit nibble to be specified. Suitable guard bands are positioned between each of the ranges within the telemetry frame to uniquely identify the synchronizing pulses, thereby avoiding undefined and erroneous data transmission.

Figure 3:
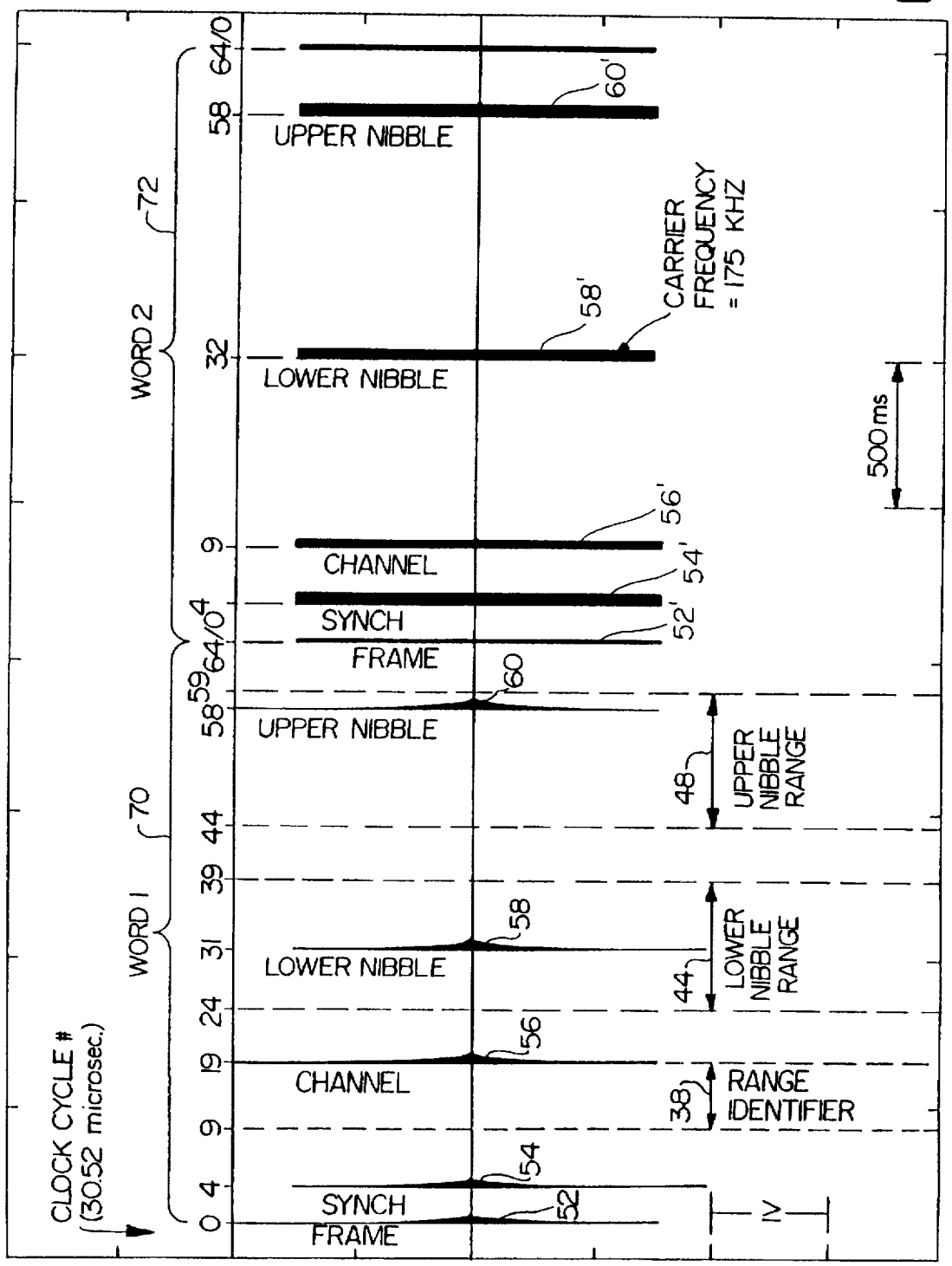
FIG. 3 is a view of a first, prior art, PPM telemetry frame without PWM and a second telemetry frame with PWM of the RF pulses of the telemetry frame.

FIG. 3 further illustrates the telemetry frame format including the PWM of the telemetry frame boundary or start, synchronization, ID, and LN and UN data RF pulses in the second of two successive telemetry frames of RF uplink 26. A first telemetry frame telemetry frame 70 corresponds to Word 1, and its RF pulses are not PWM encoded. A second telemetry frame 72 corresponds to Word 2, and its RF pulses are PWM encoded. A count of clock cycles is indicated along an upper horizontal axis of this diagram for each telemetry frame 70, 72. Each basic clock cycle has a duration of 30.52 microseconds.

The first telemetry frame 70 is initiated by a telemetry frame start RF pulse 52. A synchronization RF pulse 54 is shown uniquely identified as precisely four clock cycles later. Synchronization RF pulse 54 is used to provide telemetry frame synchronization between the uplink telemetry transmitter (i.e., IPG 10) and the receiver (i.e., programmer 20). A telemetry frame ID or "CHANNEL" RF pulse 56 is located within ID range 38, which range is defined as 9–19 basic clock cycles from the telemetry frame start RF pulse 52. In Word 1, for example, ID RF pulse 56 is located at clock cycle nineteen. This identifies the telemetry frame 70 as a particular type of data, e.g., "Sense Threshold" data, as indicated in Table 1 of the above-incorporated '404 and '319 patents.

A LN data RF pulse 58 is located within LN range 44 of twenty-four to thirty-nine basic clock cycles from telemetry frame start RF pulse 52. In Word 1, for example, LN pulse 58 is located at clock cycle thirty-one, specifying a binary value of "seven" on a scale of 0–15. A UN data RF pulse 60 is located at clock cycle fifty-eight within UN range 48, which range is defined as forty-four to fifty-nine basic clock cycles from telemetry frame start RF pulse 52, and is demodulated in similar fashion.

Guard bands of five clock cycles separate the synchronizing pulse 54 from the ID range 38 position 9 as well as upper and lower pulse positions of the ID range 38, the LN range 44, the UN range 48 and the 64 clock cycle telemetry frame end position, where the next telemetry frame start RF pulse for telemetry frame 72 is generated. Therefore, no combination of two successive RF pulses, e.g. a telemetry frame ID RF pulse 56 at maximum range position 19 and a LN data RF pulse at minimum LN range position 24 can appear to constitute a synchronization RF pulse following a telemetry frame start RF pulse.

In the above-incorporated '404 and '319 patents and related patents, each RF pulse is typically formed of an uncontrolled, but relatively fixed number of the 175 kHz clock cycles (where the fixed number may be specified within a narrow variance range). The RF pulse has a damped sinusoidal envelope shape rising from the baseline to a peak and falling back to the baseline within one clock cycle because of the inductance of the transmitter/receiver coil and an associated capacitance of the LC tank circuit.

By contrast, in accordance with the preferred embodiment of the present invention, the data transmission capacity of each telemetry frame is magnified by incorporating PWM of at least certain ones of the telemetry frame start RF pulse 52, the synchronization RF pulse 54, the ID RF pulse 56, the LN RF pulse 58, and the UN RF pulse 60. In order to retain clearly discernible telemetry frame boundaries, the PWM encoding is preferably limited to the synchronization RF pulse 54, telemetry frame ID RF pulse 56, LN RF pulse 58 and UN RF pulse 60.

Ordinarily, an uplink 26 is encoded using the PPM telemetry frame along with PWM of at least some of these RF pulses of the telemetry frame. However, in cases where the S/N ratio of the uplink 26 is determined to be the insufficient for reliable transmission or if the programmer cannot demodulate the PWM encoding, a downlink command to disable the PWM modulation and revert to simply using the telemetry frame based encoding is transmitted to the implanted medical device. In this way, the possibility of erroneously decoding the uplink 26 is diminished.

Moreover, it is preferred that the PWM is effected by selecting a number of constant amplitude, full sinusoidal pulses of a clock frequency, e.g. the 175 kHz, RF carrier, to represent a given data that may be correlated to the PPM position of the RF pulse in the telemetry frame or may be independent of the pulse position. However, the PWM may be effected using decaying sinusoidal pulses having differing numbers of full amplitude pulses or differing decay characteristics. Such pulse widths may be readily demodulated in the receiver of the external programmer, assuming an adequate S/N ratio. A simple demodulation results in pulses that vary in amplitude in proportion to the PWM as shown below with reference to FIGS. 10 and 11.

Figure 9:
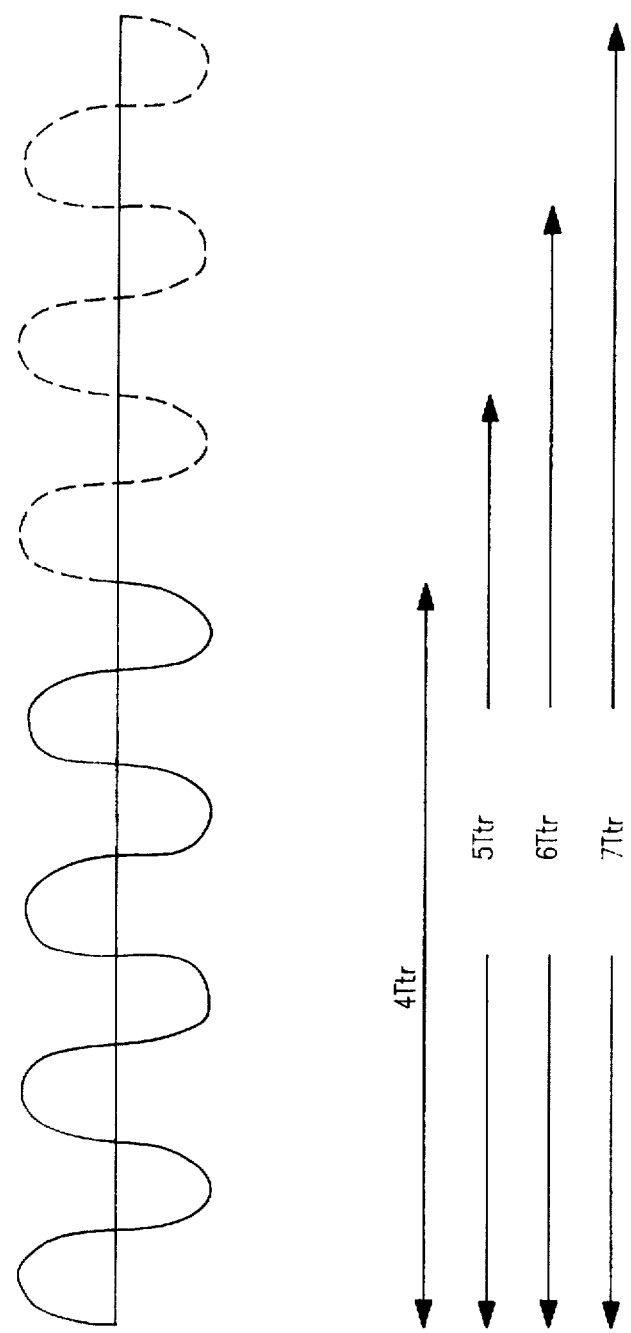
FIG. 9 illustrates PWM of whole cycles of the RF carrier in accordance with a preferred embodiment of the invention.
Figure 10:
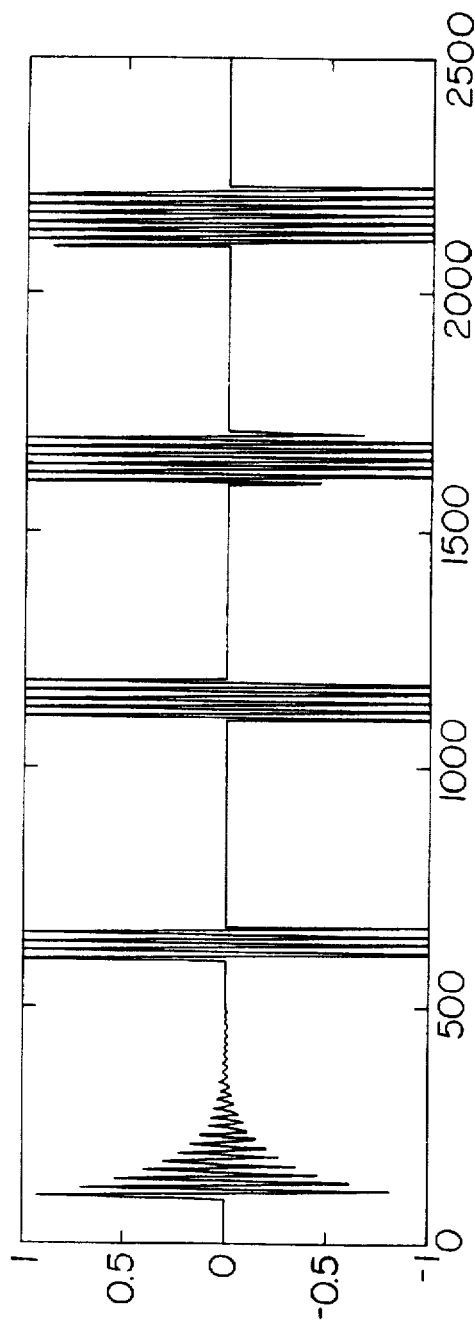
FIG. 10 is a simplified view of a series of pulse width modulated RF pulses that may be realized in the practice of the present invention.
Figure 11:
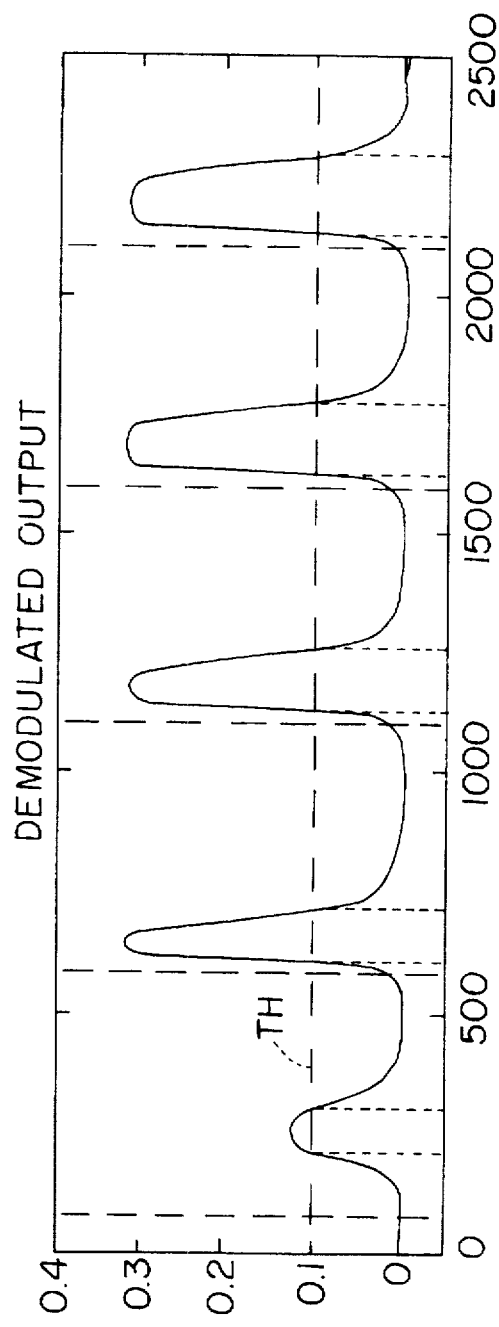
FIG. 11 is a further simplified view of the demodulation of the series of RF pulses depicted in FIG. 10 in a receiver, whereby the PWM may be decoded.

In FIG. 3, the conventional decaying sinusoidal waveforms of the RF pulses are shown in telemetry frame 70, and the PWM and square waveform of the RF pulses 54', 56', 58' and 60' in accordance with the invention are shown in telemetry frame 72 for ease of comparison. For example, UN data RF pulse 60' may be twice as wide as ID RF pulse 56', and the LN RF pulse 58' and synchronization RF pulse 54' may have intermediate pulse widths. More detailed examples of the PWM are shown in FIGS. 9–11 and described below, following the description of the telemetry transmission circuitry and operations incorporated into the implanted pulse generator 10 depicted in FIGS. 4–8.

As described in the above-incorporated '404 and '319 patents, the types of data that are included in uplink 26 include analog data having a wide range of possible values, depending on the extent that an amplitude or width of an analog signal is sampled. Consequently, the data carrying capacity of single telemetry frame, as enhanced by PWM of certain of the RF pulses of the telemetry frame in accordance with the present invention, may be fully utilized in the uplink transmission of a single analog value. As described above, a fully utilized telemetry frame can identify a single data type using one of the ID range pulse positions and can identify a great many possible analog values representing the combinations of pulse positions and pulse positions in the LN and UN ranges and pulse widths of the synchronization RF pulse, the ID RF pulse, and even the telemetry frame start or boundary RF pulse, allowing fine discrimination of analog data values. On the other hand, the transmission of a single digital signal or state may require as little as a single ID range position and a single one of the LN or UN range positions.

Figure 4:
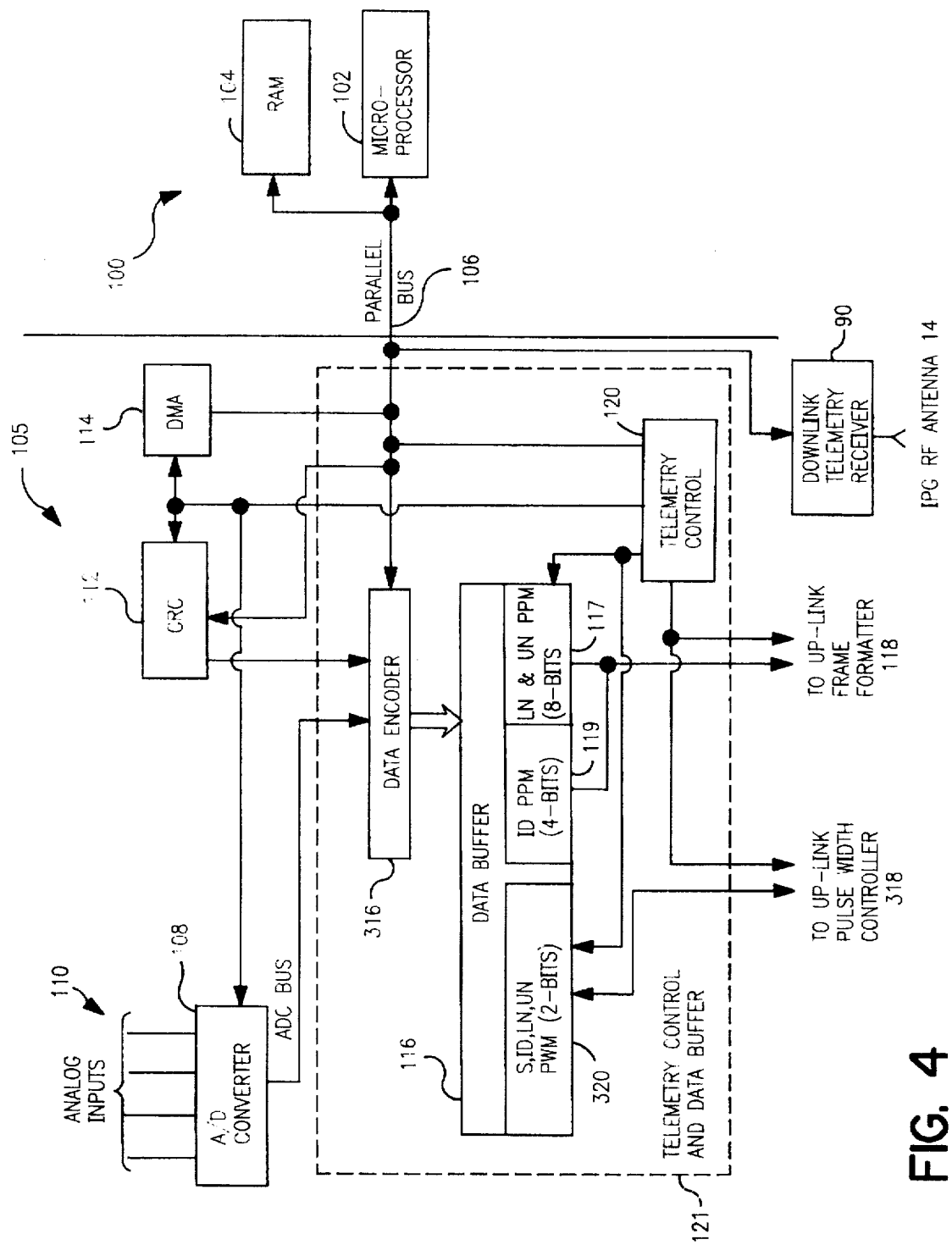
FIG. 4 is a simplified block diagram of a portion of the telemetry encoding circuitry of the implantable medical device for implementation of the improved telemetry format.

FIG. 4 is a block diagram of that portion of IPG 10 which is associated with formatting and transmission of RF uplink 26 and corresponds in large part to FIG. 4 of the above-incorporated '404 patent. FIG. 4 also depicts the IPG downlink telemetry receiver circuitry 90 which is coupled to the IPG telemetry antenna to receive and decode downlink telemetry INTERROGATE or PROGRAM commands generated in use of the external programmer 20. In typical use, the PROGRAM commands accompany downlink telemetry of new operating modes or parameter values used to control operation of the IPG 10. The INTERROGATE command is used to cause the IPG transmitter circuitry to formulate the telemetry frames of the present invention and to generate the RF pulses of the telemetry frames to uplink data from the IPG memory or other sources as described below. In accordance with the present invention, the INTERROGATE command causes the data to be encoded in PWM and PPM combinations of the RF pulses of the telemetry frame. In accordance with a second aspect of the present invention, the programmer 10 includes the error detection circuitry and functions of the above-incorporated '851 application to evaluate the telemetry uplink. In the event that the uplink signal strength is low or the noise level is high resulting in difficulty in demodulating the uplink RF pulse widths, the external programmer 10 interrupts the uplink and instructs the IPG to reduce the use of the PWM feature or to eliminate it.

Most of the unique hardware which embodies the present invention is located on a single substrate, custom chip 105. The remainder is microprocessor-based logic 100, comprising microprocessor 102, random access memory (RAM) 104, and parallel bus 106. Chip 105 has an analog-to-digital (A/D) converter 108 which receives a number of analog inputs 110 from a multiplexer (not shown). A/D converter 108 permits data to be transferred via RF uplink 26 to be digitized as necessary, e.g. in real time, so that all data is transmitted in a standardized digital form. CRC circuitry 112 generates and analyzes the cyclic redundancy code used to forward error detect telemetry data transmitted over RF uplink 26 as described in the above-incorporated '404 patent. In the preferred embodiment, it is also used for data received by IPG 10 via a downlink (not shown). DMA circuitry 114 provides direct memory access to RAM 104 is indicated at 114, thus permitting multiple byte transfers without constant management by microprocessor 102. Key hardware used to implement RF uplink 26 comprises telemetry control and data buffer circuitry 121, also depicted in FIG. 6.

Telemetry control and data buffer circuitry 121 also includes a data encoder 316 for compiling or staging ADC converted data from the ADC bus, error detect data from CRC circuitry 112 and digital data from the parallel bus 106 into telemetry frame based data sets to be transmitted in a given PPM/PWM telemetry frame. As described above, a given telemetry frame may be devoted to a single type of analog data or a plurality of digital data states or values. The data encoder 316 assembles the telemetry frame data into twenty bits that are then transferred to a data buffer 116. Data buffer 116 includes storage for twenty bits of data related to a single identified analog data type or one (or more) digital data types that may be incorporated into a given telemetry frame of the type shown in FIGS. 2 and 3. Data buffer stages are partitioned by location into an eight-bit or byte PWM section 320 for temporary storage of PWM codes and a four-bit section 119 and an eight-bit section 117 for temporary storage of PPM codes. PWM section 320 includes four two-bit code storing stages, each two-bit code signifying one of four possible pulse width values of the synchronizing (S) RF pulse, the identifying (ID) RF pulse, the LN data RF pulse, and the UN data RF pulse. PPM four-bit section 119 stores the telemetry frame identifier PPM code received from the microprocessor 102, and PPM eight-bit section 117 stores the LN and UN data value PPM codes of a telemetry frame. Data buffer 116 thus stores all of the variables for one complete PPM/PWM telemetry frame.

Telemetry control and data buffer circuitry 121 also includes telemetry control 120 that enables the commencement of an uplink telemetry session, typically in response to an instruction received from the external programmer via downlink telemetry, and also times transfer of PWM and PPM codes to uplink pulse width controller/antenna driver 318 and uplink telemetry frame formatter 118. Telemetry control 120 consists primarily of a telemetry status register that stores the telemetry commands and status as loaded by microprocessor 102.

Uplink timing or telemetry frame formatter 118 (shown in FIGS. 6 and 7) decodes the four-bit ID PPM code and the eight-bit LN/UN PPM code stored in data buffer 116 to produce a set of timing signals which key the start of each of the RF pulses of a telemetry frame described above with respect to FIGS. 2 and 3. Uplink pulse width controller/antenna driver 318 (shown in FIG. 8) decodes the two-bit S, ID, LN and UN PWM codes and controls the pulse width of the RF pulse accordingly.

Figure 5:
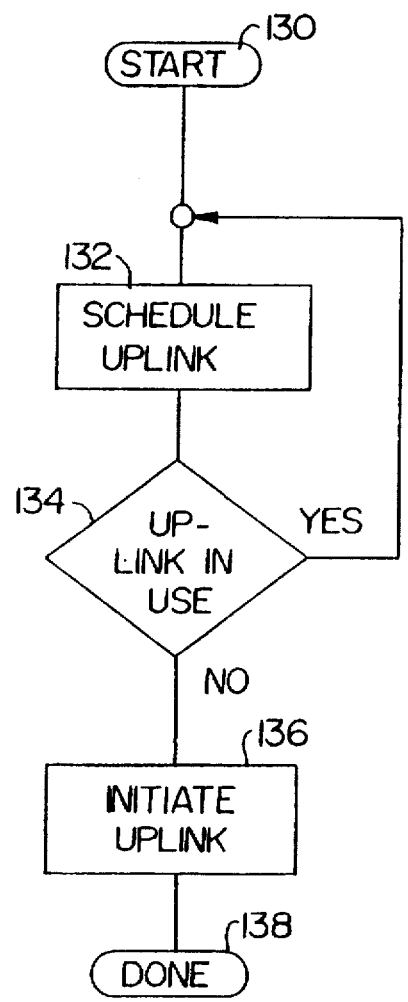
FIG. 5 is a flowchart for establishing link availability of the uplink transmission channel.

FIG. 5 is a basic flowchart showing the overall function of the microprocessor-based logic 100. The role is essentially one of initiation of the transfer, rather than management of each detail of the transmission. Software associated with RF uplink 26 is started at element 130, usually by a downlink command to transfer data. Element 132 prioritizes uplink transmission requests and schedules the requested transmissions via the uplink 26. For example, lower priority is given to continuous real time transfers, such as EGM and battery voltage, whereas higher priority is given to single occurrence transmissions of status information. After scheduling, element 134 determines whether an uplink transmission is currently in progress, and, if it is, reschedules the request. If an uplink transmission is not in progress after scheduling, element 136 initiates the uplink transmission by activating telemetry control 120. Exit is via element 138. While some additional management of the process is required during the transmission, a description of such further details has been omitted, since it is not believed necessary to one skilled in the art to fully understand the present invention. Further details including a source code listing are found in the above-incorporated '404 and '319 patents.

Figure 6:
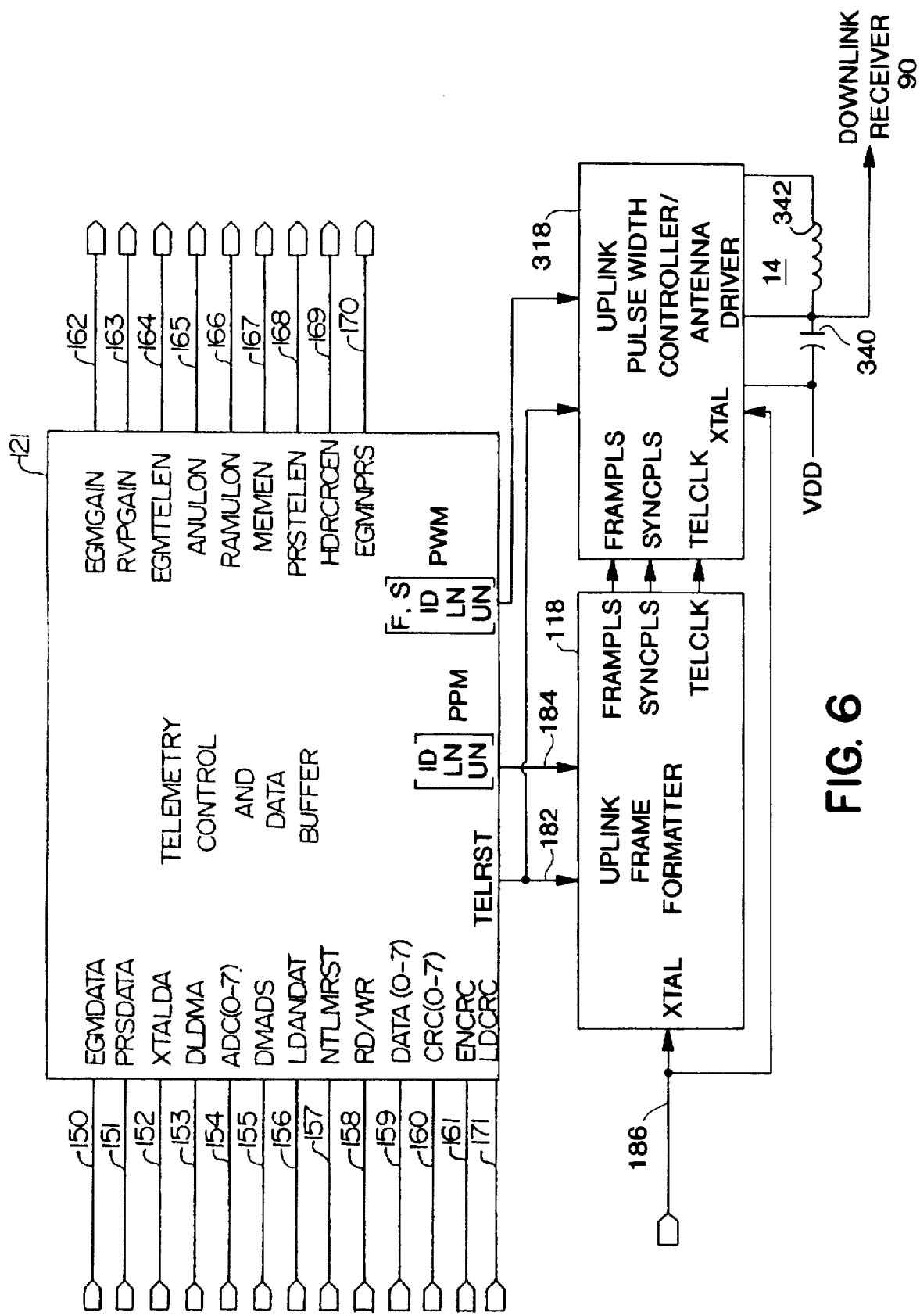
FIG. 6 is a simplified block diagram of the uplink telemetry frame formatter and the uplink pulse width controller and antenna driver.

FIG. 6 is a block diagram showing the major data and control signals of telemetry control and data buffer 121 (which includes data encoder 316, data buffer 116 and telemetry control 120 shown in FIG. 4), and also of uplink telemetry frame formatter 118 and uplink pulse width controller/antenna driver 318 in association with IPG antenna 14. A primary function of data encoder 316 and data buffer 116, as indicated above, is the encoding and staging of the twenty variable PWM and PPM defining bits of a given telemetry frame for distribution to the uplink telemetry frame formatter 118 and the uplink pulse width controller/antenna driver 318. The data is received over a parallel bus 159 and can be from any one of several sources as described above. Control lines EGMDATA 150, PRS-DATA 151, DLDMA 153, DMADS 155, LDANDAT 156, ENCRC 161, and LDCRC 171 specify sources. The output of A/D converter 108 of FIG. 4 is presented separately to data buffer 116 as an eight-bit parallel transfer to ADC(0–7) at 154 (see FIG. 6). The output of CRC 112 is presented separately to data buffer 116 as an eight-bit parallel transfer to CRC(0–7) at 160, since those devices are located on the same substrate.

Telemetry control 120 outputs a number of control signals, including EGMGAIN 162, RVPGAIN 163, EGMTELEN 164, ANULON 165, RAMULON 166, MEMEN 167, PRSTELEN 168, HDRCRCEN 169, and EGMNPRS 170, which are used to enable and control inputs to data encoder 316 and/or data buffer 116. The TELRST signal on line 182 (from telemetry control 120) resets timing in uplink telemetry frame formatter 118 and initializes the circuits to commence telemetry uplink. The TELRST signal also initiates a parallel transfer of the ID four-bit and the LN and UN eight-bit PPM codes for the upcoming telemetry frame to the uplink telemetry frame formatter 118 and the parallel transfer of the F, S, ID, LN, and UN two-bit PWM codes for the upcoming telemetry frame to uplink pulse width controller/antenna driver 318.

Figure 7:
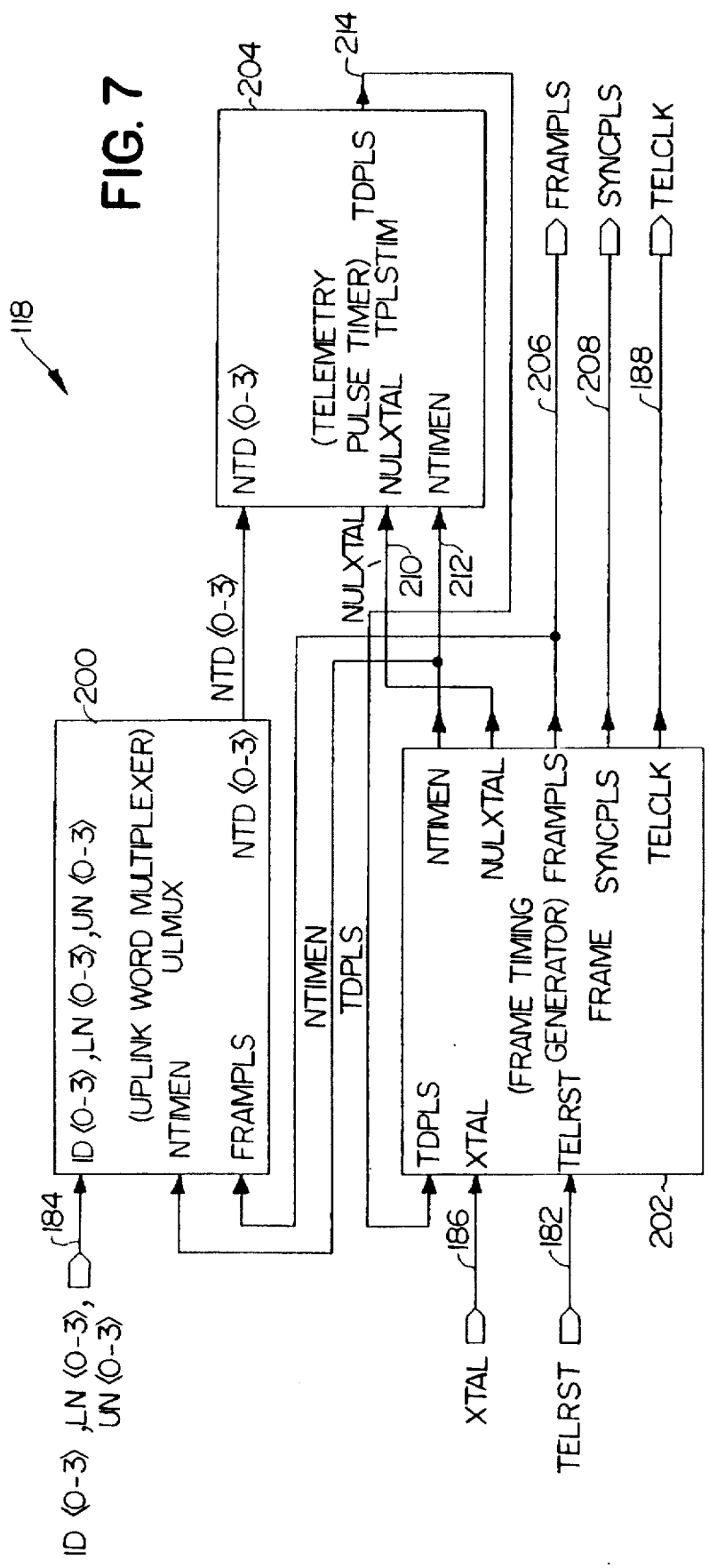
FIG. 7 is an expanded block diagram of the uplink telemetry frame formatter that performs the telemetry frame PPM formatting in accordance with the PPM codes developed in the block diagrams of FIGS. 4 and 6.

The primary function of uplink telemetry frame formatter 118 depicted in FIG. 7 is to key the transmission of 175 kHz carrier RF energy at the proper pulse start times for the telemetry frame start, telemetry frame synchronization, telemetry frame ID, LN data, and UN data RF pulses depicted in FIGS. 2 and 3. The uplink frame formatter 118 includes an uplink word multiplexer (ULMUX) 200, telemetry frame timing generator (FRAME) 202 and telemetry pulse timer (TPLSTIM) 204. In the preferred embodiment hereinabove described, each telemetry frame is comprised of sixty-four basic clock cycles defining sixty-four XTAL clock defined pulse positions starting with the telemetry frame start RF pulse. The 32.768 kilohertz crystal clock signal XTAL is supplied to FRAME 186 which synchronizes the FRAMPLS and SYNCPLS signals and the transitions of the TELCLK state to it.

The telemetry frame formatting process is initiated by receipt of the telemetry frame initiating control signal TEL-RST at input 182, which enables uplink when in a LOW state and disables uplink when in a HIGH state. When TELRST state goes LOW, and when ULMUX 200 is loaded with the four-bit ID, LN and UN PPM codes at input 184, telemetry frame timing is commenced by the generation of a FRAMPLS signal in FRAME 202. A counter in FRAME 202 counts the next four XTAL clock signals and then generates the SYNCPLS signal. The FRAMPLS signal is used in the ULMUX to refernce the start of the frame at frame position count "0". Simultaneously with the generation of the FRAMPLS and SYNCPLS signals, the HIGH-LOW state of a TELCLK signal is switched. The timing of the ID, LN and UN encoded state transitions of the TELCLK is governed by the operation of the TPLSTIM 204 which generates three successive TDPLS signals synchronized to a number of XTAL clock signals corresponding to the encoded pulse positions for the ID, LN and UN RF pulses in ULMUX 200. The TDPLS signals also trigger a state transition of the TELCLK signal. Each state transition of the TELCLK signal is detected in the antenna driver/oscillator 324 of FIG. 8 and causes an RF pulse to be generated thereby in synchronism with the XTAL clock signal.

The ID, LN and UN PPM codes stored in the ULMUX 200 are successively compared to a count of the inverted XTAL (NULXTAL) clock signal generated by the FRAME 202. The count of NULXTAL pulses is compared to the NTD input count received from the ULMUX 200, and the TDPLS pulse is generated when the counts match. The selection of the ID, LN and UN four-bit codes at the NTD input of the TPLSTIM 204 is synchronized by the NTIMEN signal and the FRAMPLS signal. Each time the counts match, the HIGH-LOW state of the TELCLK signal is switched, and an RF pulse is generated in response.

Figure 8:
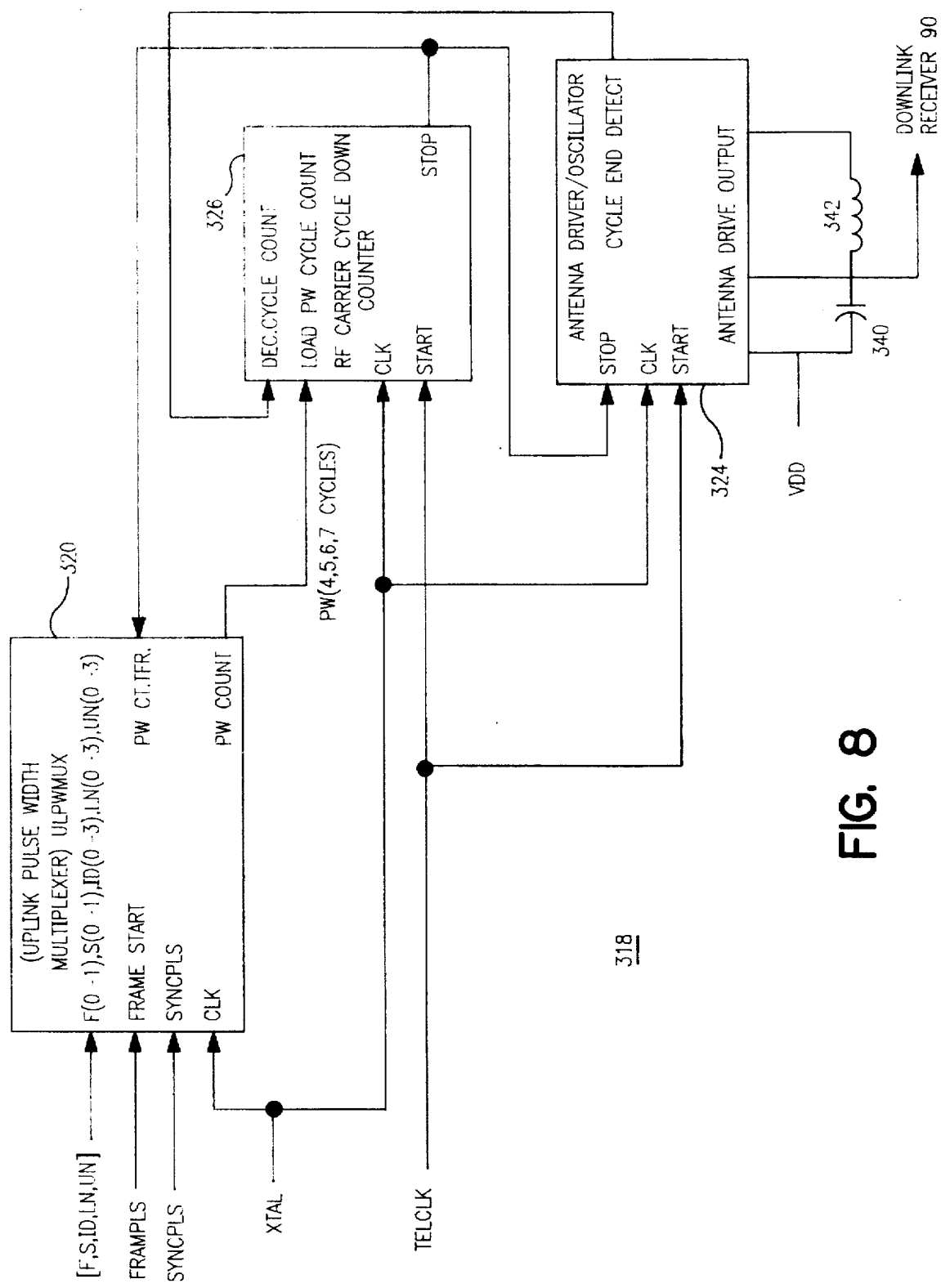
FIG. 8 is an expanded block diagram of the circuitry of the telemetry uplink pulse width controller of FIG. 6 for performing the PWM of the RF pulse generated by the RF pulse generator circuit in accordance with the PPM and PWM codes derived in the circuitry of FIG. 4.

FIG. 8 is a block diagram for the uplink pulse width controller/antenna driver 318 in association with the implantable medical device antenna capacitor 340 and coil 342 of IPG RF antenna 14 for generating the RF carrier and the RF pulses of the uplink telemetry frame having pulse widths defined by the PWM codes. The F, S, ID, LN and UN PWM codes provided to registers in the uplink pulse width multiplexer (ULPWMUX) 320 are supplied to an RF carrier cycle down counter 326 to control the number of cycles of the RF carrier in each uplink RF pulse in a given telemetry frame generated by the antenna driver/oscillator circuit 324.

As described above, the FRAMPLS and SYNCPLS signals and each TELCLK state change of each telemetry frame are generated in timed relationship in the uplink telemetry frame formatter 118 and applied to uplink pulse width controller/antenna driver 318 in real time. At the time (or slightly before) the FRAMPLS is delivered, the PWM codes, that is, the F, S, ID, LN and UN PWM codes in this embodiment, are provided from telemetry control and data buffer 121 to registers in the uplink pulse width multiplexer (ULPWMUX) 320. In one preferred embodiment, all or selected ones of the telemetry frame, synchronizing, ID, lower nibble and upper nibble RF pulses are pulse width modulated. In order to strictly maintain the timing of the synchronizing interval, the F and S PWM codes may be limited to two pulse widths, neither of which are longer than the XTAL clock signal period, e.g. the periods corresponding to 4 and 5 RF carrier cycles. The remaining ID, LN and UN RF pulses may be modulated in one of four pulse widths, e.g., the periods of 4, 5, 6 or 7 RF carrier cycles. Preferably, the two-bit or four-bit PWM codes are transformed into carrier cycle counts through use of a look up table or the like in ULPMUX 320. Each count is then transferred as a PW COUNT to the RF carrier cycle down counter 326 prior to the generation of the corresponding RF pulse in the antenna driver/oscillator 324.

The FRAMPLS and SYNCPLS signals are applied to the ULPWMUX 320 to synchronize PWM code transfers of the F and S two-bit codes to load the RF carrier cycle down counter 326 just before the corresponding RF pulse is started. The TELCLK signal is applied to the antenna driver/oscillator 324 to cause the RF pulse to be started each time the TELCLK state changes through energization of the RF antenna capacitor 340 and coil 342. The carrier cycle ends of the RF pulse carrier cycle are detected in the antenna driver/oscillator 324, and carrier cycle end signals are applied to the down counter 326 to decrement its count from the loaded PW count to zero or a further threshold count. When the count is decremented by 4, 5, 6 or 7 to the zero or threshold count, the STOP signal is generated and applied to the STOP input of the antenna driver/oscillator 324 to immediately halt generation of the RF carrier.

The ID, LN and UN two-bit codes are transferred to the RF carrier cycle down counter 326 during the guard bands in the XTAL clock cycles preceding their respective pulse position ranges. This can be accomplished in a variety of ways, including at predetermined counts of XTAL clock signals within the guard bands, if a running count is maintained in ULPWMUX 320. One way to accomplish this is to effect the transfer on the next XTAL clock signal following the generation of the STOP signal by the RF carrier cycle down counter 326.

The antenna driver/oscillator 324 may take the form of and operate in accordance with principles of operation described in the above-referenced '605 application, incorporated herein by reference. Specifically, the antenna driver/oscillator drives the RF antenna LC tank circuit comprising inductor 342 and capacitor 340 to oscillate at the 175 kHz carrier frequency employing a driver circuit that detects when the current flow is zero in each half cycle. Each half cycle and full cycle can be detected in the process of determining when zero current flow occurs in the cycle. The detected ends of full carrier cycles are preferably used to decrement the down counter 326 cycle count. The antenna driver/oscillator 324 can also be immediately stopped on a detected zero current condition, allowing the RF pulse to have a discrete number of cycles.

FIGS. 9–11 depict illustrations of the PWM waveforms of the RF pulses employed in the practice of the present invention. FIG. 9 is a simplified view of the manner of pulse width modulation wherein whole RF carrier cycles are counted in the down counter 326 as counts 4 Ttr, 5 Ttr, 6 Ttr and 7 Ttr. The RF pulse is terminated when the count is decremented to zero or a reference count as described above. The RF pulse widths correspond to 4, 5, 6 or 7 RF carrier cycles providing RF pulse widths of about 22.8 µsec to 40.0 µsec given the 175 kHz carrier period of 5.7 µsec.

In the circuit of FIG. 8, the cycles of the RF carrier frequency depicted in FIG. 9 are counted and compared against the PWM code for the particular RF pulse of the telemetry frame. The widest RF pulse of seven full cycles or 40.0 µsec exceeds the 32 kHz telemetry clock period by about 10.0 µsec, but still provides a guard band separation exceeding the 4 clock period separation between the telemetry frame start RF pulse and the synchronization RF pulse. The PWM codes for the telemetry frame and synchronization RF pulses and any RF pulses placed in the extreme maximum and minimum pulse positions of each of the ID, LN and UN PPM ranges may be prohibited or limited to the perhaps 4 and 5 RF cycles.

FIG. 10 depicts an exemplary reference decaying sinusoidal RF burst generated by ringing of the RF antenna LC circuit in the manner described in the above-incorporated '404 patent, for example, in relation to a series of full cycle RF pulses having 4, 5, 6 or 7 cycles, in accordance with the present invention. It will be observed that each of the cycles of each such RF pulse are of full amplitude and are of higher energy content than the reference decaying sinusoidal RF burst.

FIG. 11 is a simplified view of the demodulated signals resulting from demodulation in the receiver/demodulator of programmer 20 and corresponding to the series of pulse width modulated, uplink transmitted RF pulses depicted in FIG. 10. The amount of energy in the pulse width modulated RF pulses illustrated in the tracings of FIG. 10 can be detected in the signals received by the external programmer in the uplink transmission. The received RF pulses are demodulated in a receiver having a bandpass frequency characteristic that is selected to provide the relatively "squared" demodulated pulses that can be are readily discriminated in pulse width. Each demodulated pulse exhibits a pulse width that is directly proportional to the number of transmitted RF carrier cycles defining the pulse width. Even the narrowest, 4 cycle transmitted square amplitude RF pulse results in a demodulated signal amplitude that exceeds that of the damped sinusoidal RF pulse starting with the same amplitude. The pulse widths may be measured at a given threshold TH demonstrating that the transmitted RF pulses of pulse widths differing by only a single RF carrier cycle period can be distinguished readily from one another and from the conventional damped sinusoidal RF pulse.

The preferred embodiment of the present invention described above has assumed an implementation of the invention into the currently used telemetry frame-based PPM telemetry format. It will be recognized that the data encoding capacity provided by pulse width modulation of the F, S, ID, LN, and UN nibble RF pulses in a single such telemetry frame is magnified considerably. The overall telemetry transmission rate of a given uplink telemetry transmission may be increased by consolidating and encoding data in a single telemetry frame that previously required two or more telemetry frames.

Moreover, the additional data capacity of each RF pulse of the telemetry frame leads to a number of variations in the telemetry frame format that can be employed to reduce the number of pulses in a telemetry frame and/or increase the telemetry frame clock frequency without reducing the data conveyed by the telemetry frame. These variations assume the continued need for a synchronization mechanism or equivalent from which the start or end of the telemetry frame may be determined. As described above, the fixed time relation of the telemetry frame RF pulse and the synchronization RF pulse is used in order for the receiver to determine the starting point of the telemetry frame from which the ID, LN and UN RF pulse positions are timed.

In a first variation that conveys at least the same amount of data as the conventional telemetry frame 70 of RF uplink 26 depicted in FIGS. 2 and 3, a shortened telemetry frame period may be realized by diminishing the number of pulse positions of the ID range, LN range and UN range from 16 to either 8 or 4, depending on whether 2 or 4 pulse widths are employed, or to an intermediate number if 3 pulse widths are used. For example, if two pulse widths are employed in each of 8 pulse positions, or 4 pulse widths are employed in each of 4 pulse positions, then 16 data values can be demodulated from the combined pulse position and width. The telemetry frame may be reduced to 32 telemetry clock cycles from 64 clock cycles, for example, by adjustment of the ranges and the intervening guard bands.

In a further variation, the telemetry frame length 30 may be shortened and the number of RF pulses in the telemetry frame 72 including pulse width modulated RF pulses may be reduced by eliminating the ID RF pulse 36 and the ID range 38. The telemetry frame identification may be conveyed by PWM of the synchronization RF pulse 32 and/or the telemetry frame start, LN and UN RF pulses. This would eliminate dissipation of the energy of one RF pulse of the telemetry frame 72, and the telemetry frame 72 may be shortened by eliminating 16 telemetry clock cycles devoted to the ID range 38. This approach may be combined with shortening the LN and UN ranges 44 and 48 to arrive at an optimum number of telemetry clock pulses in the telemetry frame.

In a still further variation, particularly usable when the ID RF pulse and range are eliminated and the data ranges 44 and 48 are shortened, telemetry frames of differing lengths or sizes may be telemetry framed and transmitted in an intermixed manner with one another in the course of a single uplink. PWM of a telemetry frame boundary RF pulse, e.g., the telemetry frame start RF pulse $P_{TELEMETRY\ FRAME}$ may be employed to convey to the receiver that the telemetry frame contains either an eight-bit word (2 nibbles) and 32 telemetry clock cycles or a 16-bit word (4 nibbles) and 64 telemetry clock cycles, for example. The eight-bit word telemetry frame is particularly suitable for transmitting data types that relate to a binary state rather than a value within a wide range. In this manner, the overall length and elapsed time of the uplink 26 may be shortened to both conserve battery energy and minimize the risk that the uplink 26 will be disrupted by hand shaking of the RF programmer head, electrical interference or the like.

It is also contemplated in a further variation that the pulse width modulation in accordance with the present invention may be confined to the fixed position RF pulses, that is the telemetry frame boundary or start RF pulse and/or the synchronization RF pulse. In other words, a certain degree of enhanced data capacity may be achieved in a telemetry frame wherein the PPM data and the PWM data may be confined to separate telemetry frame RF pulses.

These approaches may be combined with the use of a higher telemetry clock than the above-referenced 32 kHz clock. For example, it is contemplated that a 100 kHz clock (XTAL) may be employed in formatting the telemetry frames. Wider guard bands may be required between ranges. The RF pulse position is still decoded in the receiver by measuring the time between the leading edges of the RF pulses. A first advantage of the present invention is that energy consumption and uplink transmission time may be reduced as more data can be transmitted in a single telemetry frame and/or the telemetry frame may be shortened. Another advantage lies in the compatibility of embodying PWM in the PPM telemetry frame-based telemetry format. The existing external programming equipment may be readily modified with minor hardware and software changes to accommodate the pre-existing PPM telemetry frame-based telemetry format and any of the above-described and other equivalent variations adding PWM to one or more RF pulses of the telemetry frame.

A further advantage lies in the possibility of providing the implantable medical device with the capability of formatting and transmitting the telemetry frame-based telemetry uplink in either the purely PPM telemetry frame or in one or more of the inventive variations adding PWM to one or more of the RF pulses on receipt of an instruction to do so received from the external programmer. In the course of a telemetry uplink, telemetry may be first attempted using the PWM feature, e.g., using the full number of possible RF pulse widths on the full number or selected ones of the RF pulses of the telemetry frame. Test telemetry frames of RF pulses of all of the pulse widths may be transmitted periodically to be demodulated. Electrical interference, poor quality transmission, or other disruptions evidence a low signal-to-noise ratio and/or otherwise make it not possible to demodulate all of the pulse widths. If this occurs, then the programmer may generate an error to alert the medical care giver and a downlink instruction to the implantable pulse generator to revert to use of a fewer number of the pulse widths, e.g., either 4 cycles or 7 cycles instead of 4, 5, 6 and 7 cycles. The test telemetry frames using the fewer number of RF pulse widths may then be transmitted and demodulated in the receiver of the external programmer 10. If this uplink is successfully demodulated at a suitable signal-to-noise ratio, the data to be transmitted in the uplink is then re-formatted in usable combinations of pulse width and pulse position. If the uplink is still not successful, then the programmer 10 issues a downlink telemetry instruction to the implantable medical device to abandon use of PWM and to re-format the data to be transmitted using the conventional PPM telemetry frame-based format with fixed pulse width RF pulses.

Figure 12:
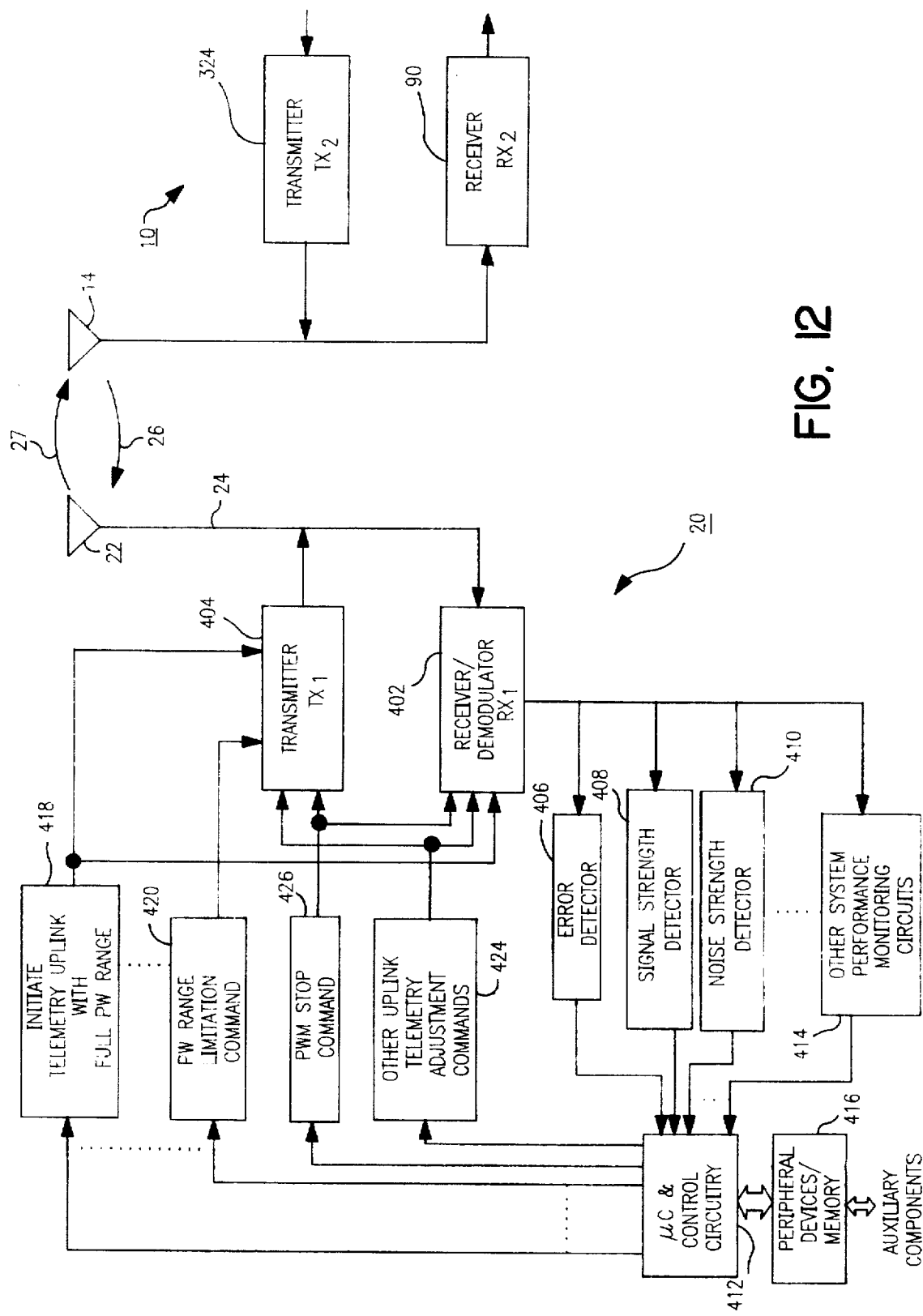
FIG. 12 is a system block diagram illustrating components of and the method of initiating a telemetry uplink and controlling the use of PWM encoding of the RF pulses of the uplink telemetry frame under adverse operating conditions.

A system in which this feature may be implemented is similar to that described in the above-incorporated '851 application and depicted in FIG. 12. As disclosed in the '851 application, system performance is monitored, and if it is found to be deficient, the IPG 10 is instructed to change the strength or other characteristics of the RF pulses of the telemetry frame. In accordance with the present invention, the instruction involves making the PWM encoding more robust or to stop using it in light of the ambient conditions. Returning to FIG. 4, the instructions received in downlink telemetry receiver 90 cause the microprocessor 102 to instruct the data encoder 316 to encode the particular RF pulses with only two distinct pulse widths, for example, or to cease any use of PWM encoding and to revert to uplink telemetry frames using fixed RF pulse widths. In the latter case, the fixed pulse width data for the F, S, ID, LN and UN RF pulses (or the alternative combinations of RF pulses described above) is still employed in the pulse width control circuitry of FIG. 8.

In FIG. 12, the method and system for controlling the transmission of the information-encoded, telemetry signals percutaneously in a telemetry uplink 26 from a transmitter 324 (and associated circuits described above) of an implanted medical device 10 to the receiver/demodulator 402 of an external device/programmer 20 as telemetry RF pulses within a telemetry frame is depicted in a functional block diagram. The external programmer 20 preferably takes the form of the MEDTRONIC® Model 9790 programmer as described above and referenced in the above-incorporated patents and patent applications assigned to Medtronic, Inc. Only the components and functions of such a programmer modified to operate to implement one form of the present invention are depicted in FIG. 12 for ease of illustration. Such a programmer 20 operates under the control of a microcomputer and control circuitry 412 which processes signals from and provides commands or signals to other dedicated circuits, e.g., the receiver/demodulator 402 and the transmitter 404 and a variety of peripheral and memory devices 416, including a keyboard, monitor or other display, printer, PCMCIA cards, hard and floppy disk drives, CD drive and the like, and other circuits. The microcomputer and control circuitry 412 also receive operator initiated INTERROGATE and PROGRAM commands that are generated when respective push-buttons on the RF programmer head are depressed or equivalent commands are received. Operating instructions for the microcomputer and control circuitry 412 are incorporated into software or firmware stored in memory. The method and system of the present invention may be incorporated into software used by such a programmer. If necessary, the pulse width discrimination function illustrated with respect to FIGS. 10 and 11 may be incorporated into circuitry of the receiver/demodulator 402 employing conventional amplitude sampling, thresholding and timing techniques.

In accordance with this aspect of the present invention, the external programmer 20 is operated by the user to initiate a telemetry uplink 26 to interrogate the memory of the implanted medical device or to otherwise transmit out real time data. The microcomputer and control circuitry 412 generates an encoded downlink command to initiate telemetry uplink with full PWM capabilities in functional block 418. The downlink command is transmitted by transmitter 404 to the implanted medical device receiver 90 to initiate a telemetry uplink to transmit the PWM and PPM encoded data telemetry frames to the external programmer receiver/demodulator 402.

The implanted medical device 10 responds to the downlink transmitted command by encoding at least one of the telemetry RF pulses of each telemetry frame in pulse width from a predetermined range of available RF pulse widths, e.g. the four pulse widths described above. As described above only one, certain ones, or all of the RF pulses of the telemetry frame may be pulse width modulated such that the PWM at least partially identifies the information being transmitted in the telemetry frame. As also described above with respect to FIG. 4, the pulse positions of the telemetry RF pulses of the telemetry frame, which are either fixed or which are encoded to be within predetermined ranges of possible pulse positions of the telemetry frame, together with the pulse width more fully identifies the information being transmitted in the telemetry frame. As also described above in detail, the telemetry frame is thereby formatted to transmit the RF pulses of the telemetry frame extending over a predetermined time interval and having a predetermined number of discrete available pulse positions for the pulse position modulated telemetry RF pulse. The telemetry uplink transmission of the telemetry frame is triggered as described above employing the telemetry clock and the PPM codes for the RF pulses. The RF pulse widths are controlled using the PWM codes to terminate the RF pulses on completion of the encoded full carrier cycles.

In the programmer 20, the uplink transmission is received and the RF pulses are demodulated in receiver/demodulator 402 to establish the start of each telemetry frame and to determine the pulse positions and pulse widths of the RF pulses of the telemetry frame. Generally speaking, the timing of occurrence and widths of uplink RF pulses are determined using amplitude and/or rise time discrimination of the signal that is received from the RF head antenna 22 and demodulated in receiver/demodulator 402. As described in the above-incorporated '851 patent, certain error detection techniques may be employed to detect errors in circuit 406, an insufficient signal strength in circuit 408 and/or a high ambient noise condition in circuit 410 or other system performance factors in circuit 414. These conditions, when present, negatively affect the capability of accurately determining the received RF pulse width. When they indicate that the capacity of accurately determining RF pulse width is compromised, the microcomputer and control circuitry 412 respond by transmitting a pulse width range limitation command 420 to the implanted medical device 10 in a telemetry downlink 27 to limit the range of RF pulse widths. For example, the pulse width range limitation command may specify that only two pulse widths that are more readily distinguishable from one another are to be used by data encoder 316 (FIG. 4) instead of the full four (or more) pulse widths. The implanted medical device 10 responds to the downlink transmitted, pulse width range limitation command by reducing the range of available RF pulse widths and repeating the encoding and generation of the PWM and PPM RF pulses of the telemetry frame in the telemetry uplink 26.

In conditions where the capability of accurately determining RF pulse width continues to be compromised, i.e., performance remains sub-standard, the microcomputer and control circuitry 412 generates a PWM stop or elimination command 426 that is transmitted to the implanted medical device 10 in a telemetry downlink 27 to limit the range of RF pulse widths to a single pulse width. The implanted medical device 10 responds to the downlink transmitted, PWM elimination command by reducing the range of available RF pulse widths to a single pulse width and repeating the telemetry uplink. Other uplink telemetry adjustment commands may be generated in the event that the system performance is still compromised or simultaneously with the steps of reducing or eliminating the use of PWM of the RF pulses as set forth above.

The PWM of the number of RF carrier cycles of between 4–7 cycles is preferred when a 32 kHz telemetry clock is employed. However, it will be understood that other numbers of whole and/or half carrier cycles may be used.

While the invention has been described above in connection with the particular embodiments and examples, one skilled in the art will appreciate that the invention is not necessarily so limited. It will thus be understood that numerous other embodiments, examples, uses and modifications of and departures from the teaching disclosed may be made as to various other systems for telemetering data to and from an implantable medical device, without departing from the scope of the present invention as claimed herein.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

What is claimed is:

1. A method for transmitting information-encoded, telemetry signals percutaneously between an implanted medical device and an external device as telemetry RF pulses within a telemetry frame comprising the steps of:
    (a) encoding at least one of the telemetry RF pulses of the telemetry frame by:
        (1) establishing a pulse width of the at least one telemetry RF pulse that partially identifies the information being transmitted in the telemetry frame; and
        (2) establishing a pulse position of the at least one telemetry RF pulse within the telemetry frame that, together with the pulse width more fully identifies the information being transmitted in the telemetry frame;
    (b) formatting the pulse positions of the telemetry frame within which at least one pulse width modulated telemetry RF pulse and at least one pulse position modulated RF pulse are to be transmitted, the telemetry frame extending over a predetermined time interval and having a predetermined number of discrete available pulse positions for the pulse position modulated telemetry RF pulse; and
    (c) triggering telemetry transmission of the telemetry frame so that the pulse position modulated RF pulse is generated at the formatted pulse position and the pulse width modulated RF pulse is generated having the established pulse width.

2. The method of claim 1, wherein the pulse width identifies one of a data type and a data value and the pulse position identifies the other of the data type and the data value.

3. The method of claim 1, wherein the pulse width and pulse position of the telemetry RF pulse uniquely identifies a data type.

4. The method of claim 1, wherein the pulse width and pulse position of the telemetry RF pulse uniquely identifies a data value.

5. The method of claim 1, wherein the pulse position modulated RF pulse is also the pulse width modulated RF pulse.

6. Apparatus for transmitting information-encoded, telemetry signals percutaneously between an implanted medical device and an external device as telemetry RF pulses within a telemetry frame comprising:

(a) means for encoding the telemetry RF pulse within the telemetry frame by:
  (1) establishing a pulse width of the at least one telemetry RF pulse that partially identifies the information being transmitted in the telemetry frame; and
  (2) establishing a pulse position of the at least one telemetry RF pulse within the telemetry frame that, together with the pulse width more fully identifies the information being transmitted in the telemetry frame;

(b) means for formatting the pulse positions of the telemetry frame within which at least one pulse width modulated telemetry RF pulse and at least one pulse position modulated RF pulse are to be transmitted, the telemetry frame extending over a predetermined time interval and having a predetermined number of discrete available pulse positions for the pulse position modulated telemetry RF pulse; and (c) means for triggering telemetry transmission of the telemetry frame so that the pulse position modulated RF pulse is generated at the formatted pulse position and the pulse width modulated RF pulse is generated having the established pulse width.

7. The apparatus of claim 6, wherein the pulse width identifies one of a data type and a data value and the pulse position identifies the other of the data type and the data value.

8. The apparatus of claim 6, wherein the pulse width and pulse position of the telemetry RF pulse uniquely identifies a data type.

9. The apparatus of claim 6, wherein the pulse width and pulse position of the telemetry RF pulse uniquely identifies a data value.

10. The apparatus of claim 6, wherein the pulse position modulated RF pulse is also the pulse width modulated RF pulse.

11. A method for transmitting data-encoded, telemetry signals percutaneously between an implanted medical device and an external device in a telemetry frame format within which at least one data RF pulse is to be transmitted, the telemetry frame extending over a predetermined time interval marked by a predetermined number of discrete pulse positions and further including at least one data RF pulse range comprising a sub-set of the discrete pulse positions for positioning the at least one data RF pulse with respect to the start of the telemetry frame, the method comprising the steps of:

providing a data source of data to be transmitted;
encoding the at least one data RF pulse within the telemetry frame to represent a data value selected from the data source by:
  (1) establishing a pulse width of the data RF pulse that partially identifies a data value being transmitted; and
  (2) establishing a pulse position of the data RF pulse at a predetermined data identifier pulse position within the sub-interval range that, together with the pulse width more fully identifies the data value being transmitted;

generating a telemetry frame boundary RF pulse to provide a time reference of the telemetry frame;
generating the at least one data RF pulse at the established pulse position within its respective sub-interval range following the telemetry frame boundary RF pulse; and
controlling the pulse width of the at least one data RF pulse, whereby the data RF pulse width and pulse position convey the encoded data value.

12. The method of claim 11, wherein the telemetry frame format includes a telemetry frame identification RF pulse within a telemetry frame identifier RF pulse range comprising a sub-set of the discrete pulse positions for positioning the telemetry frame identifier RF pulse with respect to the start of the telemetry frame and further comprising the steps of:

encoding the telemetry frame identifier RF pulse to represent a data type and a data value selected from the data source by:
  (1) establishing a pulse width of the telemetry frame identifier RF pulse that identifies one of the telemetry frame type and a data value being transmitted; and
  (2) establishing the pulse position of the telemetry frame identifier RF pulse at the predetermined data identifier pulse position within the identifier RF pulse range that identifies the other of the telemetry frame type and a data value being transmitted; and controlling the pulse width of the telemetry frame identifier RF pulse, whereby the telemetry frame identifier RF pulse width and pulse position convey the data value and data type.

13. The method of claim 11, wherein the telemetry frame format includes a telemetry frame identification RF pulse within a telemetry frame identifier RF pulse range comprising a sub-set of the discrete pulse positions for positioning the telemetry frame identifier RF pulse with respect to the start of the telemetry frame and further comprising the steps of:

encoding the telemetry frame identifier RF pulse to represent a data type selected from the data source by:
  (1) establishing a pulse width of the telemetry frame identifier RF pulse that partially identifies the telemetry frame type transmitted; and
  (2) establishing the pulse position of the telemetry frame identifier RF pulse at the predetermined data identifier pulse position within the identifier RF pulse range that further identifies the telemetry frame type being transmitted; and controlling the pulse width of the telemetry frame identifier RF pulse, whereby the telemetry frame identifier RF pulse width and pulse position convey the data type.

14. The method of claim 11, wherein the telemetry frame format includes a telemetry frame synchronization RF pulse at a predetermined pulse position within the telemetry frame and further comprising the steps of:

encoding the synchronization RF pulse to represent a telemetry frame type selected from the data source by establishing a pulse width of the telemetry frame identifier RF pulse; and controlling the pulse width of the telemetry frame identifier RF pulse, whereby the telemetry frame identifier RF pulse width and pulse position convey the data value and data type.

23

15. The method of claim 11, further comprising the steps of:
    encoding the telemetry frame boundary RF pulse to represent a telemetry frame size selected from the data source by establishing a pulse width of the telemetry frame boundary RF pulse; and
    controlling the pulse width of the telemetry frame boundary RF pulse.

16. Apparatus for transmitting data-encoded, telemetry signals percutaneously between an implanted medical device and an external device in a telemetry frame format within which at least one data RF pulse is to be transmitted, the telemetry frame extending over a predetermined time interval marked by a predetermined number of discrete pulse positions and further including at least one data RF pulse range comprising a sub-set of the discrete pulse positions for positioning the at least one data RF pulse with respect to the start of the telemetry frame, the apparatus comprising:
    a data source of data to be transmitted;
    means for encoding the at least one data RF pulse to represent a data value selected from the data source by:
        (1) establishing a pulse width of the data RF pulse that partially identifies a data value being transmitted; and
        (2) establishing a pulse position of the data RF pulse at a predetermined data identifier pulse position within the sub-interval range that, together with the pulse width more fully identifies the data value being transmitted;
    means for generating a telemetry frame boundary RF pulse to provide a time reference of the telemetry frame;
    means for generating the telemetry frame identifier RF pulse and the at least one data RF pulse at the established pulse positions within the respective telemetry frame identifier RF pulse range and the data RF pulse range following the telemetry frame boundary RF pulse; and
    means for controlling the pulse width of the at least one data RF pulse, whereby the data RF pulse width and pulse position convey the encoded data value.

17. The apparatus of claim 16, wherein the telemetry frame format includes a telemetry frame identification RF pulse within a telemetry frame identifier RF pulse range comprising a sub-set of the discrete pulse positions for positioning the telemetry frame identifier RF pulse with respect to the start of the telemetry frame and further comprising:
    means for encoding the telemetry frame identifier RF pulse to represent a data type and a data value selected from the data source by:
        (1) establishing a pulse width of the telemetry frame identifier RF pulse that identifies one of the telemetry frame type and a data value being transmitted; and
        (2) establishing the pulse position of the telemetry frame identifier RF pulse at the predetermined data identifier pulse position within the identifier RF pulse range that identifies the other of the telemetry frame type and a data value being transmitted; and
    said controlling means is operable to control the pulse width of the telemetry frame identifier RF pulse to the established pulse width, whereby the telemetry frame identifier RF pulse width and pulse position convey the data value and data type.

18. The apparatus of claim 16, wherein the telemetry frame format further includes a telemetry frame identifier

24

RF pulse within a telemetry frame identifier RF pulse range comprising a sub-set of the discrete pulse positions for positioning the telemetry frame identifier RF pulse with respect to the start of the telemetry frame and further comprising:
    means for encoding the telemetry frame identifier RF pulse to represent a data type selected from the data source by:
        (1) establishing a pulse width of the telemetry frame identifier RF pulse that partially identifies the telemetry frame type transmitted; and
        (2) establishing the pulse position of the telemetry frame identifier RF pulse at the predetermined data identifier pulse position within the identifier RF pulse range that further identifies the telemetry frame type being transmitted; and
    said controller means is operable to control the pulse width of the telemetry frame identifier RF pulse to the established pulse width, whereby the telemetry frame identifier RF pulse width and pulse position convey the data type.

19. The apparatus of claim 16, further comprising:
    means for encoding the telemetry frame boundary RF pulse to represent a telemetry frame size selected from the data source by establishing a pulse width of the telemetry frame boundary RF pulse; and
    said controller means is operable to control the pulse width of the telemetry frame boundary RF pulse to the established pulse width, whereby the telemetry frame boundary RF pulse width conveys the telemetry frame size.

20. Apparatus for transmitting information-encoded, telemetry RF pulses percutaneously between an implanted medical device and an external device comprising:
    a data bit source for telemetry frame identifier and data to be transmitted in a telemetry frame;
    a data encoder for encoding the telemetry frame identifier and data of each telemetry frame into data-encoded RF pulse width defining code and RF pulse position defining code;
    clock means for providing clock signals at preset clock intervals for use in defining pulse positions of the telemetry frame;
    a telemetry frame formatter responsive to the clock means and the data-encoded RF pulse position defining code for generating RF pulse trigger signals at a synchronization RF pulse position, at an encoded telemetry frame identifier RF pulse position within a telemetry frame identifier range of possible telemetry frame identifier RF pulse positions and at an encoded data RF pulse position within a data range of possible data RF pulse positions;
    an RF pulse generator responsive to the RF pulse trigger signals for generating an RF pulse at each of the synchronization RF pulse position, the telemetry frame identifier RF pulse position, and the data RF pulse position; and
    an RF pulse width controller responsive to the data-encoded pulse width defining code from the data encoder for controlling the RF pulse width in at least certain ones of the RF pulses.

21. The apparatus of claim 20, wherein:
    said telemetry frame formatter generates a telemetry frame boundary RF pulse trigger signal and said synchronization RF pulse trigger signal at a fixed pulse position in the telemetry frame in fixed time relation with respect to the telemetry frame boundary RF pulse trigger signal; and said RF pulse generator is responsive to said telemetry frame boundary RF pulse trigger signal and said synchronization RF pulse trigger signal for generating respective telemetry frame boundary RF pulses and synchronizing RF pulses in fixed time relation with respect to one another from which the start of a new telemetry frame may be decoded.

22. The apparatus of claim 20, wherein the combination of pulse width and pulse position of the telemetry frame identifier RF pulse uniquely identifies a data type.

23. The apparatus of claim 20, wherein the combination of pulse width and pulse position of the data RF pulses uniquely identify a data value.

24. The apparatus of claim 20, wherein the combination of pulse width and pulse position of the telemetry frame synchronization RF pulse identifies one of the data type and the data value.

25. A method for transmitting information-encoded, telemetry signals percutaneously between an implanted medical device and an external device as telemetry RF pulses within a telemetry frame comprising a predetermined number of pulse positions, the method comprising the steps of:

providing a source of data to be transmitted;

encoding the data into a PPM code for positioning at least certain telemetry RF pulses at pulse positions of the telemetry frame and a PWM code for establishing the pulse widths of at least certain telemetry RF pulses of the telemetry frame;

formatting the telemetry frame from the PPM code;

generating the telemetry RF pulses at the formatted pulse positions within the telemetry frame; and controlling the pulse widths of the telemetry RF pulses in accordance with the PWM code for the selected telemetry RF pulses.

26. The method of claim 25, wherein all of the telemetry RF pulses of the telemetry frame are encoded in pulse width with a PWM code.

27. The method of claim 25, wherein at least one telemetry RF pulse of the telemetry frame is encoded in pulse width with a PWM code identifying the data encoded and transmitted in the telemetry frame.

28. The method of claim 25, wherein at least one telemetry RF pulse of the telemetry frame is encoded in pulse width with a PWM code identifying the telemetry frame length.

29. The method of claim 25, wherein at least one telemetry RF pulse of the telemetry frame is encoded in pulse width with a PWM code identifying the number of data RF pulses in the telemetry frame.

30. Apparatus for transmitting information-encoded, telemetry signals percutaneously between an implanted medical device and an external device as telemetry RF pulses within a telemetry frame comprising a predetermined number of pulse positions, the apparatus comprising:

a data source for providing data to be transmitted;

encoder means for encoding the data into a PPM code for positioning at least certain telemetry RF pulses at pulse positions of the telemetry frame and a PWM code for establishing the pulse widths of at least certain telemetry RF pulses of the telemetry frame;

telemetry frame formatting means for formatting the telemetry frame from the PPM code;

generator means for generating the telemetry RF pulses at the formatted pulse positions within the telemetry frame; and pulse width controller means for controlling the pulse widths of the telemetry RF pulses in accordance with the PWM code for the selected telemetry RF pulses.

31. The apparatus of claim 30, wherein all of the telemetry RF pulses of the telemetry frame are encoded in pulse width with a PWM code.

32. The apparatus of claim 30, wherein at least one telemetry RF pulse of the telemetry frame is encoded in pulse width with a PWM code identifying the data encoded and transmitted in the telemetry frame.

33. The apparatus of claim 30, wherein at least one telemetry RF pulse of the telemetry frame is encoded in pulse width with a PWM code identifying the telemetry frame length.

34. The apparatus of claim 30, wherein at least one telemetry RF pulse of the telemetry frame is encoded in pulse width with a PWM code identifying the number of data RF pulses in the telemetry frame.

35. A method for controlling the transmission of information-encoded, telemetry signals percutaneously in a telemetry uplink from a transmitter of an implanted medical device to the receiver of an external device as telemetry RF pulses within a telemetry frame in response to telemetry commands received from the external device in a telemetry downlink, the method comprising the steps of:

from the external device, effecting a telemetry downlink to the implanted medical device; and transmitting a command to the implanted medical device to initiate a telemetry uplink to transmit encoded data telemetry frames to the external device; and in the implanted medical device, responding to the downlink transmitted command by;

(1) encoding at least one of the telemetry RF pulses of each telemetry frame by:

from a predetermined range of available RF pulse widths, establishing a pulse width of the at least one telemetry RF pulse that partially identifies the information being transmitted in the telemetry frame; and establishing a pulse position of the at least one telemetry RF pulse within a predetermined range of possible pulse positions of the telemetry frame that, together with the pulse width more fully identifies the information being transmitted in the telemetry frame;

(2) formatting the pulse positions of the telemetry frame within which at least one pulse width modulated telemetry RF pulse and at least one pulse position modulated RF pulse are to be transmitted, the telemetry frame extending over a predetermined time interval and having a predetermined number of discrete available pulse positions for the pulse position modulated telemetry RF pulse; and (3) triggering telemetry transmission of the telemetry frame so that the pulse position modulated RF pulse is generated at the formatted pulse position and the pulse width modulated RF pulse is generated having the established pulse width.

36. The method of claim 35 further comprising the steps of:

in the external device, receiving and demodulating the at least one RF pulse of the telemetry frames of the telemetry uplink from the implanted medical device to derive both pulse position and pulse width of the at least one RF pulse of the telemetry frame;

monitoring the capability of determining the pulse width by application of the telemetry uplink RF pulse width demodulation; and in conditions where the capability of accurately determining RF pulse width is compromised, transmitting a pulse width range limitation command to the implanted medical device in a telemetry downlink to limit the range of RF pulse widths; and in the implanted medical device, responding to the downlink transmitted, pulse width range limitation command by reducing the range of available RF pulse widths and repeating steps (1)–(3).

37. The method of claim 36 further comprising the steps of:

in the external device, receiving and demodulating the at least one RF pulse of the telemetry frames of the telemetry uplink from the implanted medical device to derive both pulse position and pulse width of the at least one RF pulse of the telemetry frame;

monitoring the capability of determining the pulse width by application of the telemetry uplink RF pulse width demodulation; and in conditions where the capability of accurately determining RF pulse width continues to be compromised, transmitting a pulse width modulation elimination command to the implanted medical device in a telemetry downlink to limit the range of RF pulse widths; and in the implanted medical device, responding to the downlink transmitted, pulse width modulation elimination command by reducing the range of available RF pulse widths to a single pulse width and repeating steps (1)–(3).

38. The method of claim 35 further comprising the steps of:

in the external device, receiving and demodulating the at least one RF pulse of the telemetry frames of the telemetry uplink from the implanted medical device to derive both pulse position and pulse width of the at least one RF pulse of the telemetry frame;

monitoring the capability of determining the pulse width by application of the telemetry uplink RF pulse width demodulation; and in conditions where the capability of accurately determining RF pulse width is compromised, transmitting a pulse width modulation elimination command to the implanted medical device in a telemetry downlink to limit the range of RF pulse widths; and in the implanted medical device, responding to the downlink transmitted, pulse width modulation elimination command by reducing the range of available RF pulse widths to a single pulse width and repeating steps (1)–(3).

39. Apparatus for controlling the transmission of information-encoded, telemetry signals percutaneously in a telemetry uplink from a transmitter of an implanted medical device to the receiver of an external device as telemetry RF pulses within a telemetry frame in response to telemetry commands received from the external device in a telemetry downlink, the apparatus comprising:

in the external device, means for effecting a telemetry downlink to the implanted medical device; and means for transmitting a command to the implanted medical device to initiate a telemetry uplink to transmit encoded data telemetry frames to the external device; and in the implanted medical device, means responding to the downlink transmitted command including;

(1) means for encoding at least one of the telemetry RF pulses of each telemetry frame by:

from a predetermined range of available RF pulse widths, establishing a pulse width of the at least one telemetry RF pulse that partially identifies the information being transmitted in the telemetry frame; and establishing a pulse position of the at least one telemetry RF pulse within a predetermined range of possible pulse positions of the telemetry frame that, together with the pulse width more fully identifies the information being transmitted in the telemetry frame;

(2) means for formatting the pulse positions of the telemetry frame within which at least one pulse width modulated telemetry RF pulse and at least one pulse position modulated RF pulse are to be transmitted, the telemetry frame extending over a predetermined time interval and having a predetermined number of discrete available pulse positions for the pulse position modulated telemetry RF pulse; and (3) means for triggering telemetry transmission of the telemetry frame so that the pulse position modulated RF pulse is generated at the formatted pulse position and the pulse width modulated RF pulse is generated having the established pulse width.

40. The apparatus of claim 39, further comprising:

in the external device, means for receiving and demodulating the at least one RF pulse of the telemetry frames of the telemetry uplink from the implanted medical device to derive both pulse position and pulse width of the at least one RF pulse of the telemetry frame;

means for monitoring the capability of determining the pulse width by application of the telemetry uplink RF pulse width demodulation; and means operable in conditions where the capability of accurately determining RF pulse width is compromised for transmitting a pulse width range limitation command to the implanted medical device in a telemetry downlink to limit the range of RF pulse widths; and wherein:

said encoding means in said implanted medical device is responsive to the downlink transmitted, pulse width limitation command by reducing the range of available RF pulse widths and repeating the telemetry uplink transmission using the reduced range of available RF pulse widths.

41. The apparatus of claim 40, further comprising:

in the external device, means for receiving and demodulating the at least one RF pulse of the telemetry frames of the telemetry uplink from the implanted medical device to derive both pulse position and pulse width of the at least one RF pulse of the telemetry frame;

means for monitoring the capability of determining the pulse width by application of the telemetry uplink RF pulse width demodulation; and means operable in conditions where the capability of accurately determining RF pulse width continues to be compromised for transmitting a pulse width modulation elimination command to the implanted medical device in a telemetry downlink to limit the range of RF pulse widths; and in the implanted medical device, means responsive to the downlink transmitted, pulse width modulation elimination command for reducing the range of available RF pulse widths to a single pulse width and repeating the telemetry uplink transmission using the single RF pulse width.

42. The apparatus of claim 39, further comprising:

in the external device, means for receiving and demodulating the at least one RF pulse of the telemetry frames of the telemetry uplink from the implanted medical device to derive both pulse position and pulse width of the at least one RF pulse of the telemetry frame;

means for monitoring the capability of determining the pulse width by application of the telemetry uplink RF pulse width demodulation; and means operable in conditions where the capability of accurately determining RF pulse width is compromised for transmitting a pulse width modulation elimination command to the implanted medical device in a telemetry downlink to limit the range of RF pulse widths; and in the implanted medical device, means responsive to the downlink transmitted, pulse width modulation elimination command for reducing the range of available RF pulse widths to a single pulse width and repeating the telemetry uplink transmission using the single RF pulse width.

\* \* \* \* \*